(12) United States Patent
Oren et al.

(10) Patent No.: US 8,765,702 B2
(45) Date of Patent: Jul. 1, 2014

(54) COMPOSITION AND METHODS FOR MODULATING CELL PROLIFERATION AND CELL DEATH

(75) Inventors: Moshe Oren, Rehovot (IL); Nina Raver-Shapira, Rehovot (IL); Efi Marciano, Holon (IL); Yael Spector, Tel-Aviv (IL)

(73) Assignees: Rosetta Genomics Ltd., Rehovot (IL); Yeda Research and Development Company Ltd., Rehovot (IL)

( * ) Notice: Subject to any disclaimer, the term of this patent is extended or adjusted under 35 U.S.C. 154(b) by 0 days.

(21) Appl. No.: 12/528,690

(22) PCT Filed: Feb. 26, 2008

(86) PCT No.: PCT/IL2008/000243
§ 371 (c)(1),
(2), (4) Date: Sep. 30, 2009

(87) PCT Pub. No.: WO2008/104974
PCT Pub. Date: Sep. 4, 2008

(65) Prior Publication Data
US 2010/0104662 A1    Apr. 29, 2010

Related U.S. Application Data

(60) Provisional application No. 60/903,526, filed on Feb. 27, 2007.

(51) Int. Cl.
C12N 15/11 (2006.01)
A61K 48/00 (2006.01)
C07H 21/02 (2006.01)
C07H 21/04 (2006.01)

(52) U.S. Cl.
USPC .................................. 514/44 A; 536/24.5

(58) Field of Classification Search
None
See application file for complete search history.

(56) References Cited

U.S. PATENT DOCUMENTS

| | | | |
|---|---|---|---|
| 5,034,506 | A | 7/1991 | Summerton et al. |
| 5,235,033 | A | 8/1993 | Summerton et al. |
| 6,506,559 | B1 | 1/2003 | Fire et al. |
| 2005/0107325 | A1 | 5/2005 | Manoharan et al. |
| 2005/0182005 | A1 | 8/2005 | Tuschl et al. |
| 2006/0105360 | A1 | 5/2006 | Croce et al. |

FOREIGN PATENT DOCUMENTS

| | | |
|---|---|---|
| EP | 2111408 | 7/2008 |
| WO | WO 93/23569 | 11/1993 |
| WO | WO 94/02595 | 2/1994 |
| WO | WO 99/04819 | 2/1999 |
| WO | WO 99/05094 | 2/1999 |
| WO | WO 2005/013901 A2 | 2/2005 |
| WO | WO 2005/078139 A2 | 8/2005 |

(Continued)

OTHER PUBLICATIONS

Kunz-Schughart et al. Journal of Biomolecular Screening, 2004, 9:273-285.*

(Continued)

Primary Examiner — Terra Cotta Gibbs
(74) Attorney, Agent, or Firm — Polsinelli PC; Teddy C. Scott, Jr.; Ron Galant

(57) ABSTRACT

Described herein are compositions and methods for modulation of p53-dependent cell death and cell proliferation. The compositions are microRNAs and associated nucleic acids.

3 Claims, 31 Drawing Sheets

(56) References Cited

FOREIGN PATENT DOCUMENTS

| WO | WO 2005/118806 A2 | 12/2005 |
|---|---|---|
| WO | 2006/137941 | 12/2006 |
| WO | WO 2006/137941 A2 | 12/2006 |
| WO | WO 2007/016548 A2 | 2/2007 |
| WO | 2008/088858 | 7/2008 |

OTHER PUBLICATIONS

Crooke et al Annu. Rev. Med., 2004, vol. 55, pp. 61-95.*
Agrawal et al., Molecular Med. Today, 6: 72-81.*
Branch et al Trends in Biochem Sci, 1998, 23, 45-50.*
Kelland et al European Journal of Cancer, 2004, 40, 827-836.*
Barad et al.., "MicroRNA expression detected by oligonucleotide microarrays: System establishment and expression profiling in human tissues", Genome Research, 2004, vol. 14, pp. 2486-2494.
Bartel et al., "MicroRNAs: At the Root of Plant Development?", Plant Physiology, Jun. 2003, vol. 132, pp. 709-717.
Bartel, "MicroRNAs: Genomics, Biogenesis, Mechanism, and Function", Cell, Jan. 23, 2004, vol. 116, pp. 281-297.
Berezikov et al., "Phylogenetic Shadowing and Computational Identification of Human microRNA Genes", Cell, Jan. 14, 2005, vol. 120, pp. 21-24.
Brennecke et al., "Principles of MicroRNA—Target Recognition", PLoS Biology, Mar. 2005, vol. 3, Issue 3, e85.
Cimmino et al., "miR-15 and MiR-16 induce apoptosis by targeting BCL2", Proc. Natl. Acad. Sci., USA, Sep. 27, 2005, vol. 102, No. 39, pp. 13944-13949.
Doench et al., "Specificity of microRNA target selection in translational repression", Genes & Development, 2004, pp. 1-8.
Hofacker et al., "Fast Folding and Comparison of RNA Secondary Structures", Monatshefte. f. Chemie, 1994, vol. 125, pp. 167-188.
Krek et al., "Combinatorial microRNA target predictions", Nature Genetics, Apr. 3, 2005, pp. 1-6.
Krutzfeldt et al., "Silencing of microRNAs in vio with 'antagomirs'", Nature, vol. 438, pp. 685-689.
Lewis et al., "Conserved Seed Pairing, Often Flanked by Adenosines, Indicates that Thousands of Human Genes are microRNA Targets", Cell, Jan. 14, 2005, vol. 120, pp. 15-20.
Raver-Shapira et al., "Transcriptional Activation of MiR-34a Contributes to p53-Mediated Apoptosis", Molecular Cell, Jun. 8, 2007, vol. 26, pp. 1-12.
Soutschek et al., "Therapeutic silencing of an endogenous gene by systemic administration of modified siRNAs", Nature, Nov. 2004, vol. 432, pp. 173-178.
Welch et al., "MicroRNA-34a functions as a potential tumor suppressor by inducing apoptosis in neuroblastoma cells", Oncogene, Jul. 26, 2007, vol. 26, No. 34, pp. 5017-5022.
Xi et al., "Differentially Regulated Micro-RNAs and Actively Translated Messenger RNA Transcripts by Tumor Suppressor p53 in Colon Cancer", Clinical Cancer Research, Apr. 2, 2006, vol. 12, No. 7, pp. 2014-2024.
Yekta et al., "MicroRNA-Directed Cleavage of HOXB8 mRNA", Science, Apr. 23, 2004, vol. 34, pp. 594-596.
"Human DNA sequence from clone RP3-510D11 on chromosome 1p36. 2-36.3 Contain two novel genes, the H6PD gene for hexose-6-phosphate dehydrogenase (glucose-1-dehydrogenase)(FLJ22807 and two CpG islands", EMBL Accession No. Z98044 (Jul. 23, 1997).
Brown at al., Geneseq. Accession No. AEP46207, "Human hsa-mir-specific micro RNA sequence" SEQ ID No. 58 (Mar. 8, 2007).
Brown et al., Geneseq. Accession No. AEE99366, "Human miRNA sequence, hsa-mir-34a" (Dec. 15, 2005).
Clark, EMBL Accession No. AL591166, "Human DNA sequence from clone RP11-315013 on chromosome 1" (May 4, 2001).
Croce, Geneseq Accession No. AES70619, "Human miR gene product sequence, SEQ ID No. 79" (Feb. 8, 2007).
Esau et al., Geneseq Accession No. ADX029025 "Human primary microRNA (pri-mRNA) mir-34)" (Feb. 17, 2005).
Wakamatsu et al., EMBL Accession No. DB286351, "*Homo sapiens* cDNA clone UTERU30140985 5' end mRNA sequence" (Oct. 23, 2005).
International Search Report dated Sep. 15, 2008, PCT/IL2008/000243.
Wiggins JF, et al. Development of a Lung Cancer Therapeutic Based on the Tumor Suppressor MicroRNA-34. Cancer Res, 2010;70(14):OF1-8.
Hollstein, Monica, et al., p53 Mutations in Human Cancers, Jul. 5, 1991: 49-53.
Raver-Shapira, Nina, et al., Transcriptional Activation of miR-34a Contributes to p53-Mediated Apoptosis, Molecular Cell, 2007; 26: 731-743.
Raver-Shapira, Nina, et al., Tiny Actors, Great Roles MicroRNAs in p53's Service, Cell Cycle, 2007; 6(21): 2656-2661.
Welch, C., et al., MicroRNA-34a functions as a potential tumor suppressor by inducing apoptosis in neuroblastoma cells, Oncogene, 2007; 26: 5017-5022.
Goldschneider, David, et al., Expression of C-terminal deleted p53 isoforms in neuroblastoma, Nucleic Acids Research, 2006; vol. 34, No. 19: 5603-5612.
Karpinich, Natalie O., et al., The Course of Etoposide-Induced Apoptosis in Jurkat Cells Lacking p53 and Bax, Journal of Cellular Physiology, 2006; 208: 55-63.
Lu, Jun, et al., MicroRNA expression profiles classify human cancers, Nature, Jun. 9, 2005: vol. 435; 834-838.
Tazawa, Hiroshi, et al., Tumor-suppressive miR-34a induces senescence-like growth arrest through modulation of the E2F pathway in human colon cancer cells, PNAS, 2007; vol. 104; No. 39:15472-15477.
Kyriazis, Andreas P., et al., Growth Patterns and Metastatic Behavior of Human Tumors Growing in Athymic Mice, Cancer Research, 1978; vol. 38: 3186-3190.
Beckman, Mary, MicroRNAs Found Cavorting With p53, JNCI, 2007; vol. 99; Issue 22: 2007: 1664-1665.
Product Information Sheet for ATCC CRL-5803, American Type Culture Collection, 1-3.
Opposition against European Patent No. 2126078 filed Jan. 10, 2013.
U.S. Appl. No. 60/880,919, filed Jan. 17, 2007.
M.Higashiyama et al., MDM2 gene amplification and expression in non*small* cell lung cancer: immunohistochemical expression of its protein is a favourable prognostic marker in patients without p53 protein accumulation, British Journal of Cancer, 1997;75(9):1302-8.
A.M.Gonzalez-Angulo et al., p53 expression as a prognostic marker in inflammatory breast cancer, Clin. Cancer Res., 2004;10:6215-21.
T.Megha, p53 mutation in breast cancer. Correlation with cell kinetics and cell of origin, J. Clin. Pathol., 2002;55:461-5.
E.Piaton et al., p53 immunodetection of liquid-based processed urinary samples helps to identify bladder tumours with a higher risk of progression, British Journal of Cancer, 2005;93:242-7.
N.F.S.Watson et al., Evidence that the p53 negative / Bcl-2 positive phenotype is an independent indicator of good prognosis in colorectal cancer: A tissue microarray study of 460 patients, World Journal of Surgical Oncology, 2005;3:47.

* cited by examiner

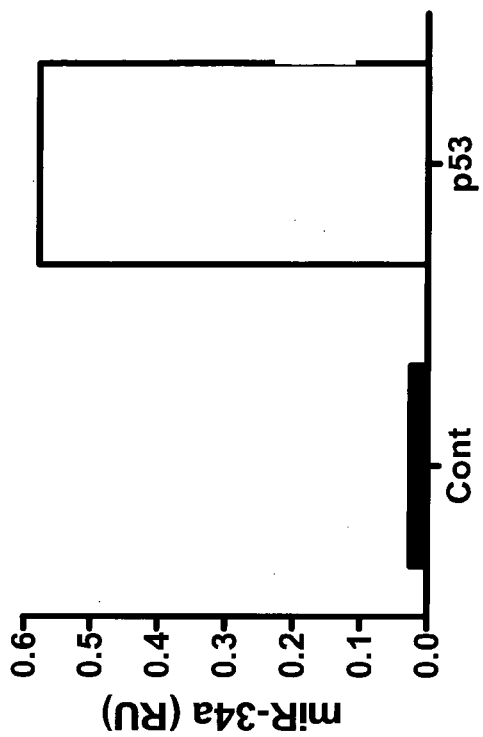
Figure 2C
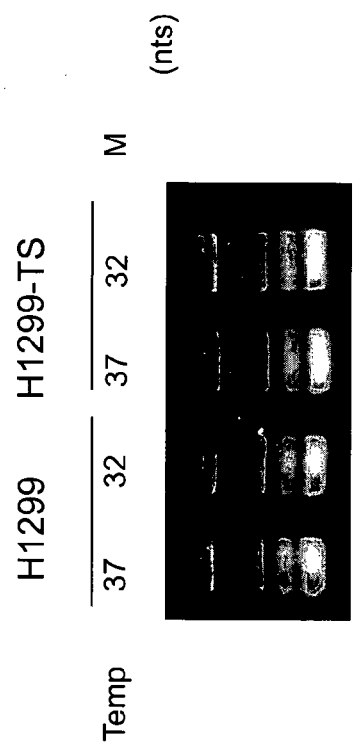
Figure 2B

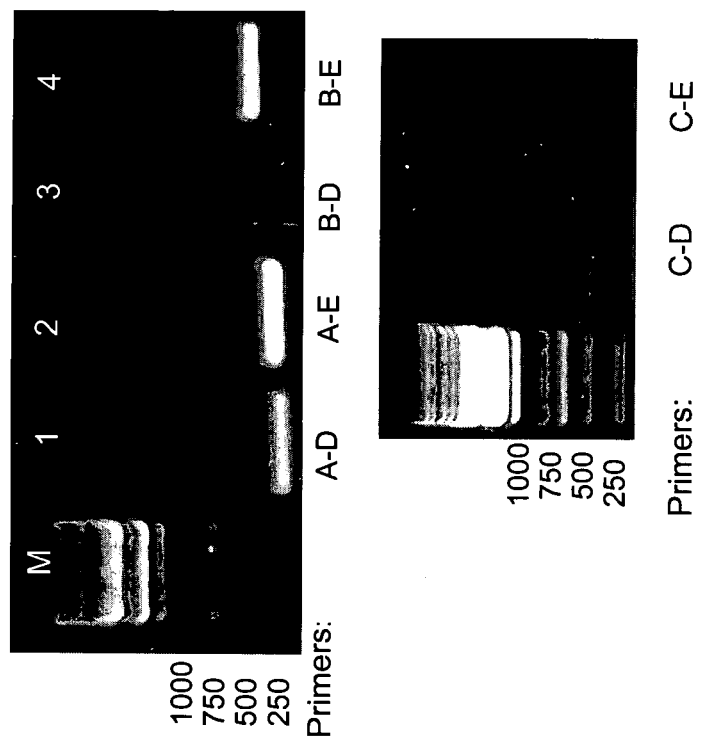

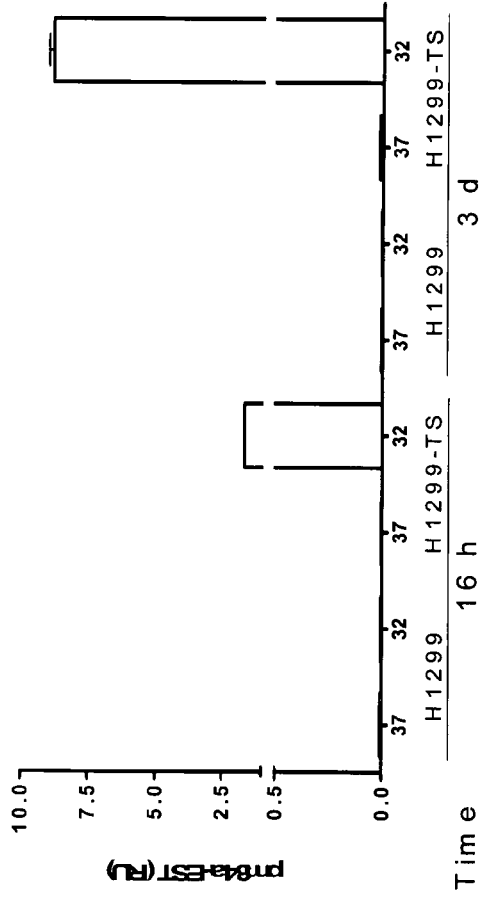
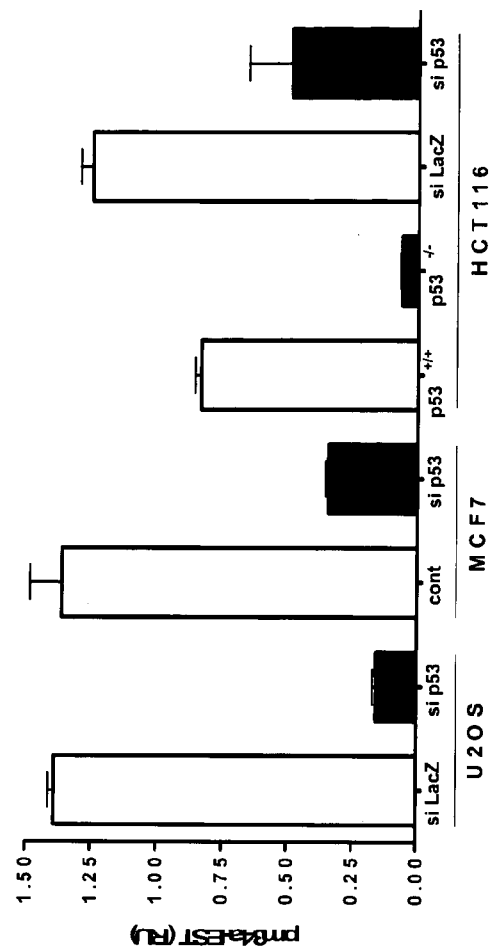
Figure 3D
Figure 3E

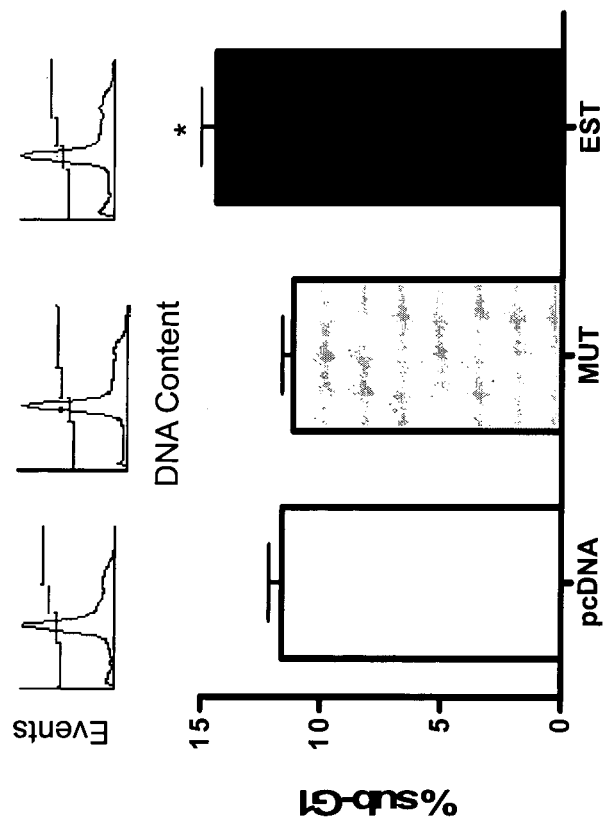
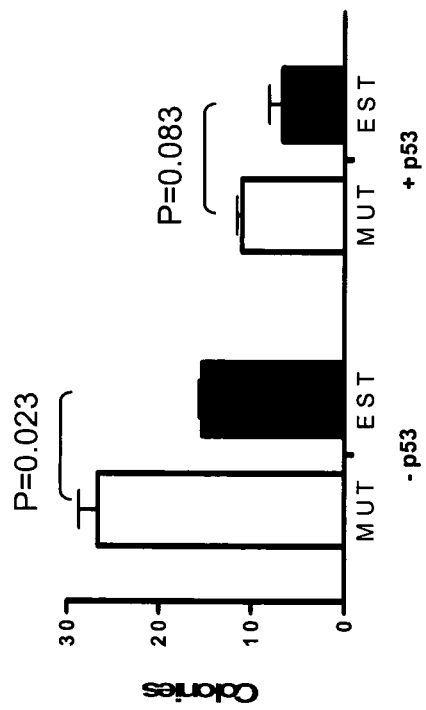
Figure 6E
Figure 6F

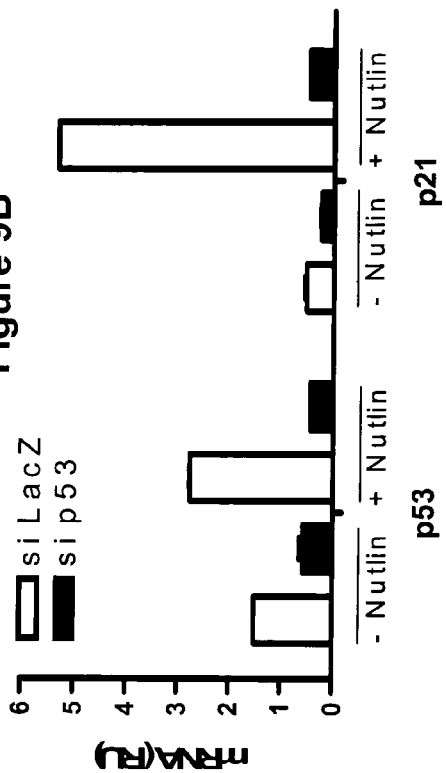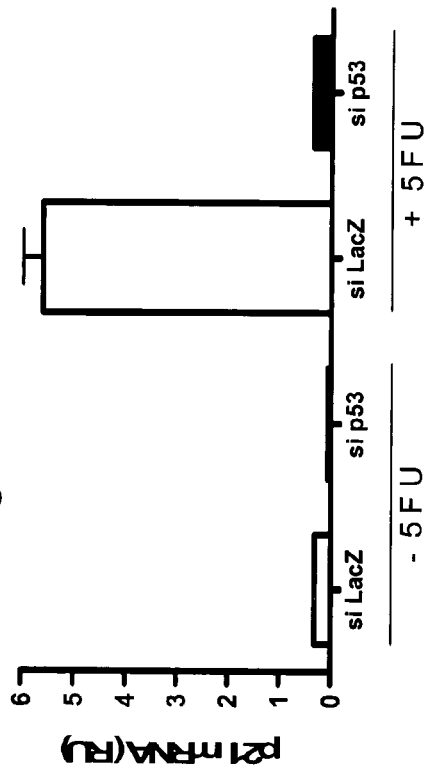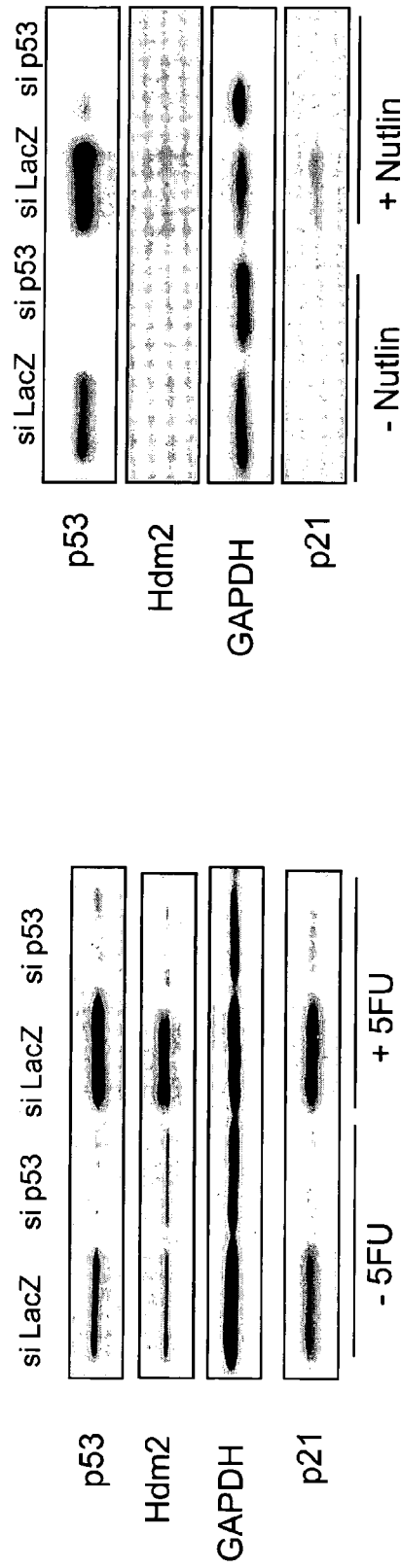
Figure 9A, Figure 9B, Figure 9C, Figure 9D

Figure 12A

```
1    ATGCGCCCTGCCTGGCCCCCACCTGTCCTCTTTCCTTTTCAGGTGGAGGAGATGCCGCT
1     M  R  P  A  W  P  P  P  G  P  L  S  F  S  G  G  G  D  A  A

61   GTCCCGTCGGTCTGGGGACAGCCCCAGCTCCCCCGGATCCCCGGAGAGACGCGTCGCG
21    V  P  S  V  W  G  Q  P  S  S  P  D  P  G  L  E  R  R  V  A

121  GCCCCGGGGGCCTGGTGGCACGAGCAGGAAGGAGACCCGGCGGCGGCTCTGCCTGGGCT
41    A  P  G  P  G  G  T  S  R  K  E  D  P  A  A  G  S  A  W  A

181  TGCCTGGGCTTGTTCCGAGCCGGGCTGCTTCTCGGTGACCACGCAGATCGGGGCATTTG
61    C  L  G  L  F  R  A  G  L  L  L  G  D  H  A  D  R  G  H  L

241  GAGATTTGCGGGAGTCCTGCAGCCAAGCCCGGGCAGGAGAGGCCTGAAGCCTGCAC
81    E  I  L  R  E  S  C  S  Q  A  P  G  Q  E  R  P  G  S  L  H

301  TACCTGCTCGCCCCGTCCCAGCATGCACCCAGGTGCTGGGGAGAGGCAGGACAGGCCTGT
101   Y  L  L  A  P  S  Q  H  A  P  R  C  W  G  E  A  G  Q  A  C

361  CCCCCGAGTCCCCTCCGGATGCCGTGGACCGGCCAGCTGTGAGTGTTTCTTTGGCAGTGT
121   P  P  S  P  L  R  M  P  W  T  G  Q  L  *

421  CTTAGCTGGTTGTTGTGAGCAATAGTAAGGAAGCAATCAGCAAGTATACTGCCCTAGAAG

481  TGCTGCACGTTGTGGGCCCAAGAGGGAAGATGAAGCGAGAGATGCCCA
```

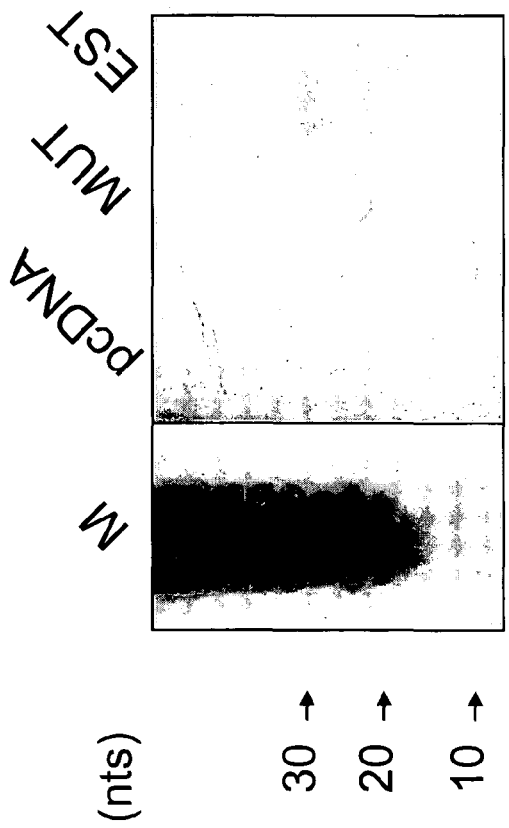

| Duplex of hsa-miR-34a and Jagged 1 (JAG1) The microRNA seed is in bold (positions 2-8) | Position on the 3' UTR of JAG1 (RefSeq accession NM_000214) | Genomic location of binding site (NCBI Build 36.1, hg18 assembly, March 2006) | SEQ ID NO |
|---|---|---|---|
| ```
            TTTG  - -   G   T                 T
       5' A     CCA  TA AG ACACTGCC       3' JAG1
       3' T     GGT  AT TC TGTGACGG       5' hsa-miR-34a
            TGTT  CG   -   -               T
``` | 1287 - 1310 | Chromosome 20, the minus strand, positions: 10566837 - 10566859 | JAG1: SEQ ID NO 38 hsa-miR-34a: SEQ ID NO 1 |
| ```
         - -  G   - - - G G   G
       5' CA   ACC GC   G CACTGCC  3' JAG1
       3' GT   TGG CG   C GTGACGG  5' hsa-miR-34a
         TT -    T ATT T    T
``` | 1 - 19 | Chromosome 20, the minus strand, positions: 10568127 - 10568145 | JAG1: SEQ ID NO 39 hsa-miR-34a: SEQ ID NO 1 |

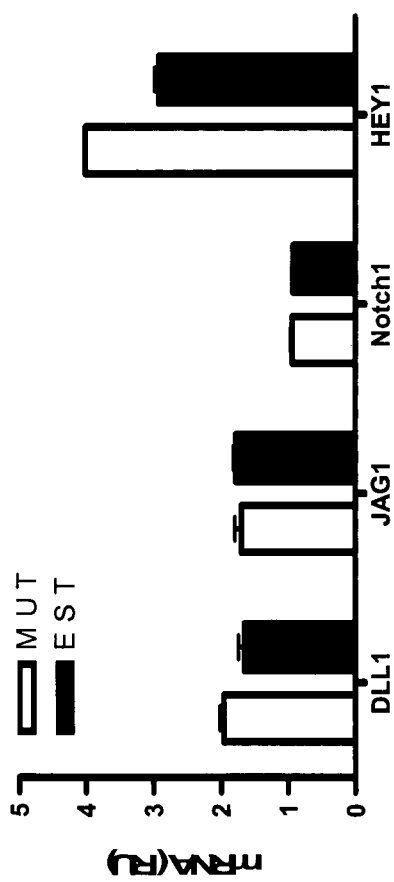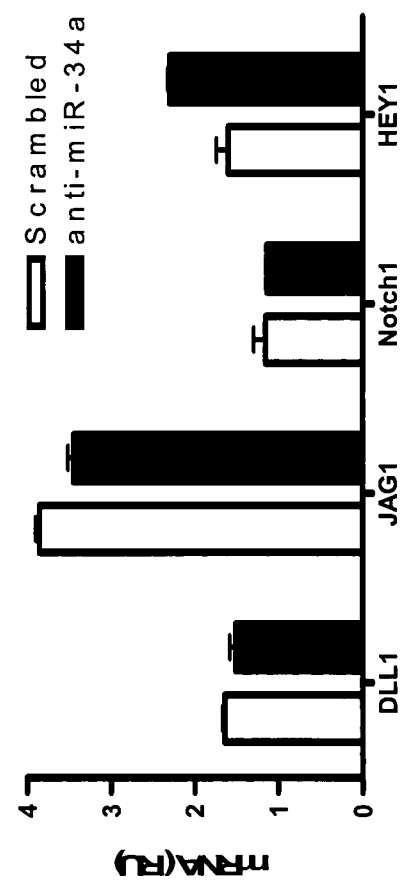

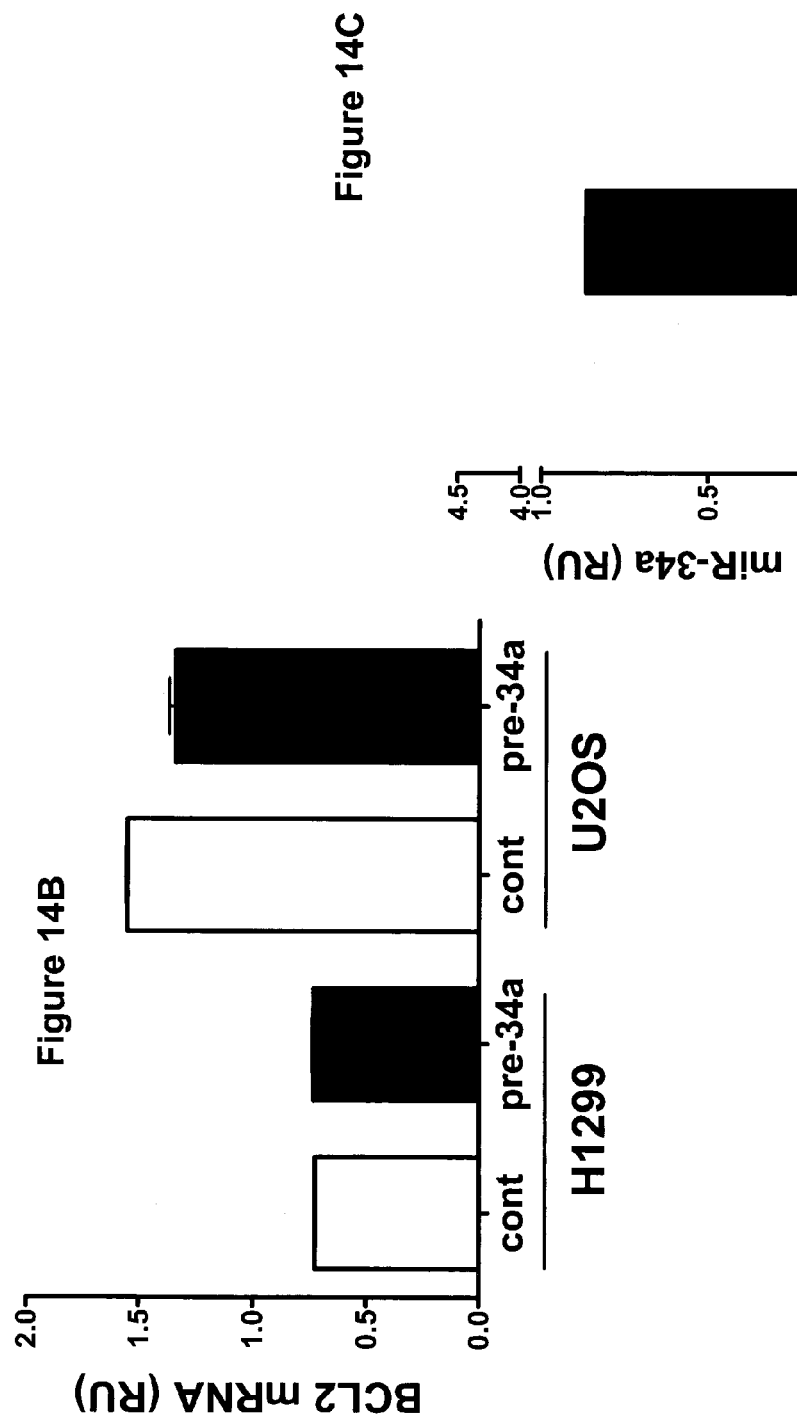

COMPOSITION AND METHODS FOR MODULATING CELL PROLIFERATION AND CELL DEATH

CROSS-REFERENCES TO RELATED APPLICATIONS

This is the national stage of International Application No. PCT/IL2008/000243, filed on Feb. 26, 2008, which claims the benefit of U.S. Provisional Patent Application No. 60/903,526, filed Feb. 27, 2007, the contents of which are incorporated herein by reference.

FIELD OF THE INVENTION

The invention relates to compositions and methods for modulation of p53-dependent cell death and cell proliferation. The compositions are microRNAs and associated nucleic acids.

BACKGROUND OF THE INVENTION

In recent years, microRNAs (miRNAs, miRs) have emerged as an important novel class of regulatory RNA, which has profound impact on a wide array of biological processes. These small (typically 18-24 nucleotides long) non-coding RNA molecules can modulate protein expression patterns by promoting RNA degradation, inhibiting mRNA translation, and also affecting gene transcription. MiRs play pivotal roles in diverse processes such as development and differentiation, control of cell proliferation, stress response and metabolism. There are currently about 700 known human miRs, and their number probably exceeds 800.

The expression of many miRs was found to be altered in numerous types of human cancer, and in some cases strong evidence has been put forward in support of the conjecture that such alterations may play a causative role in tumor progression. Cancer-associated changes in miR expression patterns can be brought about by various genetic and epigenetic mechanisms. Most notably, a number of transcription factors whose activity is altered in cancer cells, including c-myc and E2F, were found to regulate the RNA polymerase II-dependent transcription of the precursors of particular miRs. Hence, the oncogenic effects of these transcription factors may be mediated not only by modulation of protein-coding mRNA levels but also by specific changes in miR expression.

The p53 protein is a sequence-specific transcription factor that functions as a major tumor suppressor in mammals. p53 is activated in response to a variety of stress signals, including genotoxic damage, dysfunction of the mitotic apparatus, aberrant activation of oncogenes, oxidative stress, nutrient deprivation and more. The activated p53 can dictate a plethora of biochemical and biological outcomes, ranging from effective repair of minor damage all the way to cessation of cell cycle progression and induction of replicative senescence and apoptotic cell death. Inactivation of the tumor suppressor function of p53 is one of the most frequent genetic alterations in human cancer, and close to half of all human tumors carry p53 gene mutations within their cells.

As a transcription factor, p53 can increase or repress the transcription of many hundreds of protein-encoding genes, and this ability is believed to underlie in great part its tumor suppressor functions.

To date there has been no definitive description of any miR whose expression is directly regulated by p53, or of the functional consequences of such regulation.

In view of the important role of cell death in developmental processes, in normal function and in the pathogenesis of diverse diseases and conditions, there is an increasing need for novel methods of modulating cell death in cell populations and for compositions that may be effectively employed in such methods.

SUMMARY OF THE INVENTION

According to the present invention, the expression of several miRs (SEQ ID NOS: 1-9) was altered by p53 activation. The invention demonstrates for the first time that the gene encoding the pri-mIR-34a (SEQ ID NO: 10) is a direct transcriptional target of p53. Positive regulation of transcription by p53 is mediated via a strong p53 binding site (p53BS) (SEQ ID NO: 11), located within the transcribed region of the pri-mIR-34a gene.

The present invention discloses the finding that miR-34a (SEQ ID NO: 1) possess antiproliferative and proapoptotic activities, thereby contributing to the tumor suppressor effects of activated p53.

The invention provides compositions and methods for treating, preventing or diagnosing of a disease or disorder associated with the p53 gene, including but not limited to cancer, neurodegenerative disorder and infectious disease.

An isolated nucleic acid is provided. The nucleic acid may comprise a sequence of a p53-regulated microRNA. The nucleic acid may comprise a sequence encoding a pri-micoRNA being regulated by p53. The nucleic acid may comprise a sequence of 18-530 nucleotides in length of any of SEQ ID NOS: 10-11, 38-41, the complementary sequence thereof, or a sequence at least 80% identical thereto.

The nucleic acid may have a sequence as set forth in any of SEQ ID NOS: 10-11, 38-41. The nucleic acid may comprise a modified base.

A probe comprising the nucleic acid, wherein said nucleic acid is labeled, is also provided.

A composition comprising the probe is also provided. A biochip comprising the probe is also provided.

A vector comprising the nucleic acid of the invention and a promoter for expression in mammalian cells is also provided. A host cell comprising the nucleic acid is also provided.

A pharmaceutical composition comprising as active ingredient one or more nucleic acids of the invention or the expression vector encoding the latter is also provided.

The pharmaceutical composition may be administered in combination with at least one other anticancer agent in unit dosage form. The anticancer agent is selected from the group consisting of cisplatin, carboplatin, camptothecins, doxorubicin, cyclophosphamide, etoposide, vinblastine, Actinomycin D and cloposide.

A method for modulating cell death in a population of cells is also provided. The method may comprise modifying the level of expression of a nucleic acid sequence selected from the group consisting of SEQ ID NOS: 1-11, 46-54, a complementary sequence thereto, or a sequence at least about 80% identical thereto. Said cells are selected from the group consisting of tumor cells; cells of the immune system; hematopoietic progenitor cells; embryonic cells; cells of the nervous system; and cells infected with intracellular pathogens.

A method of inhibiting cell proliferation is also provided. The method may comprise introducing into cells, a nucleic acid sequence selected from the group consisting of SEQ ID NOS: 1-8, 10, 46-54 or a sequence at least about 80% identical thereto.

A method of preventing or treating cancer in a subject in need thereof is also provided. The method may comprise administering to the subject an effective amount of a composition comprising a nucleic acid sequence selected from the group consisting of SEQ ID NOS:1-8, 10, 46-54 or a sequence at least about 80% identical thereto. Said cancer, including but not limited to non-small cell lung carcinoma, prostate carcinoma, renal carcinoma, colon carcinoma, ovarian carcinoma, breast carcinoma, pancreatic carcinoma, Li-Fraumeni syndrome (LFS), osteosarcoma, squamous cell carcinoma, adenocarcinoma and melanoma.

A method of preventing or treating a disease or disorder associated with the p53 gene comprising administering to a subject in need thereof or to cells harvested from said subject an effective amount of a composition comprising a microRNA capable of down-regulating JAG1 (gi|4557678) or Bcl-2 (gi|72198188) is also provided. The microRNA may be selected from the group consisting of SEQ ID NOS: 1-8, or a sequence at least about 80% identical thereto.

A method of inducing tumor cell death or inhibiting tumor cell proliferation in a subject in need thereof is also provided. The method may comprise administering to the subject a therapeutically effective amount of a composition comprising a nucleic acid sequence selected from the group consisting of SEQ ID NOS:1-8, 10, 46-54 or a sequence at least about 80% identical thereto.

A method of preventing or treating a neurodegenerative disease in a subject in need thereof is also provided. The method may comprise administering to the subject an effective amount of a composition comprising a nucleic acid sequence selected from the group consisting of a complementary sequence of SEQ ID NOS:1-8, 10, 46-54 or a sequence at least about 80% identical thereto. Said neurodegenerative disease, including but not limited to Alzheimer's disease and Parkinson's disease.

A method of preventing or treating an infectious disease in a subject in need thereof is also provided. The infectious disease is caused by a pathogenic microorganism selected from the group consisting of a virus, a bacterium, a fungus and a protozoan. Said infectious disease including but not limited to HIV infection, cytomegalovirus infection, herpesvirus infection, and papillomavirus infection.

A method of diagnosing a subject with a disease or disorder associated with the p53 gene is also provided. Said disorder or disease is selected from the group consisting of cancer, neurodegenerative disorder and infectious disease.

The method may comprise providing a biological sample from the subject and measuring the level of a nucleic acid sequence selected from the group consisting of SEQ ID NOS: 1-10, 46-54 wherein a level of the nucleic acid different from a control is indicative of said disorder or disease.

A method for identifying a compound that modulates expression of a proapoptotic or antiproliferative miRNA is also provided. The method may comprise providing a cell that is capable of expressing the nucleic acid sequence of any of SEQ ID NOS: 10-11, 38-41; a complementary sequence thereof, or a sequence at least 80% identical thereto; contacting the cell with a candidate modulator; and measuring the level of expression of the proapoptotic miRNA, wherein a difference in the level of said miRNA compared to a control identifies the compound as a modulator.

The use of a nucleic acid comprising a nucleic acid sequence selected from the group consisting of SEQ ID NOS: 1-8, 10, 46-54; a complementary sequence thereof, or a sequence at least about 80% identical thereto for the manufacture of a medicament for the treatment or prevention of a disease or disorder associated with the p53 gene, is also provided.

These and other embodiments of the present invention will become apparent in conjunction with the figures, description and claims that follow.

Figure 1:
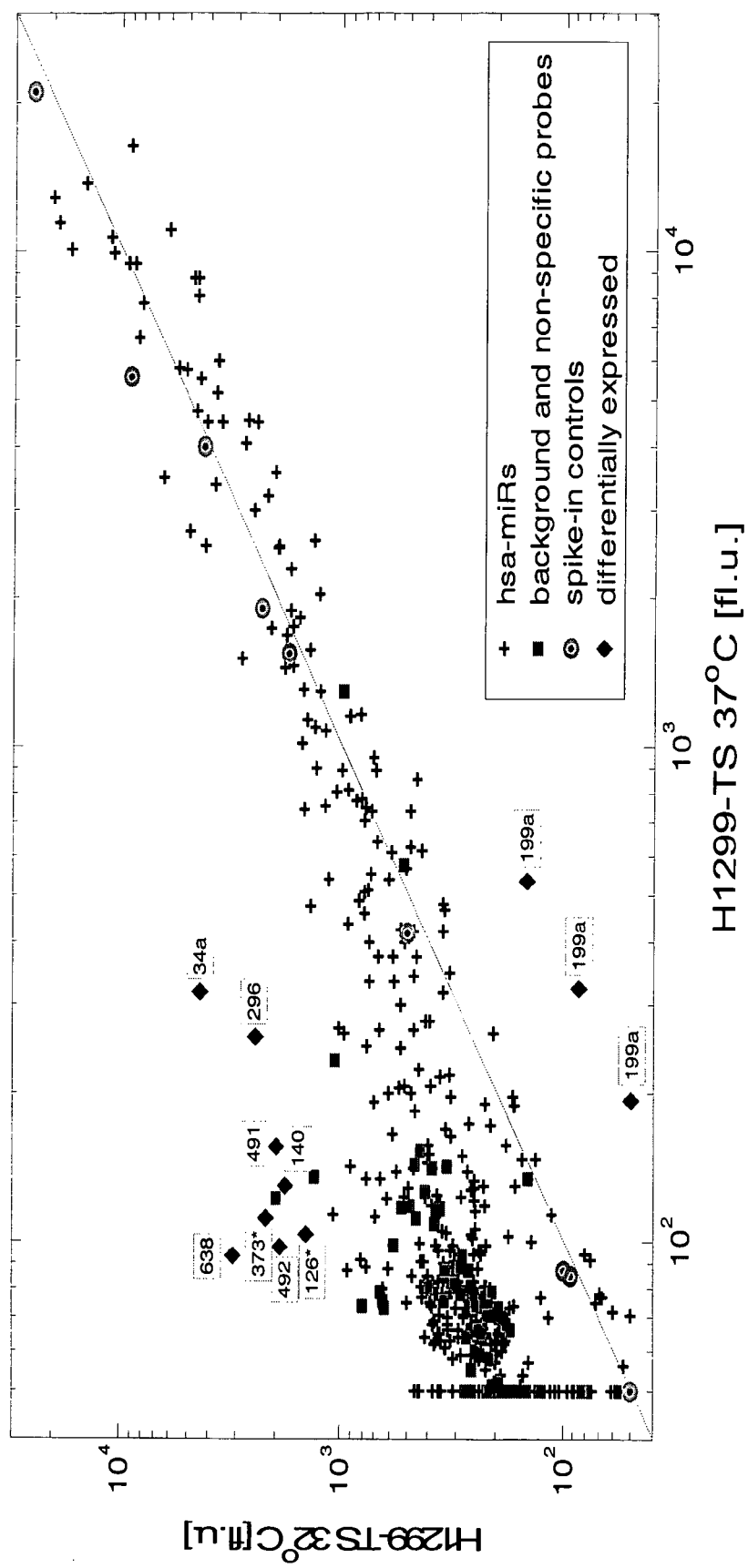
FIG. 1 shows miR expression profiling of H1299-TS using miRdicator™ array. 15 µg of total RNA extracted from H1299-TS cell lines cultured at the permissive (32° C.) or restrictive (37° C.) temperatures were ligated to Cy3 and hydridized overnight on two miRdicator™ arrays. Data is presented in arbitrary fluorescence units (fl.u.). Crosses represent signals for all human miRs; magenta squares represent background and non-specific probes. Circles represent signals of synthetic spike-in controls, and diamonds indicate human miRs which showed notable differential expression. Each miR-probe was spotted in triplicate and each data point in the figure represents at least 2 spots that fall within ±14% of the value indicated (or ±100 fl.u. for low signals), and none being further off than ±73% of this value (or ±300 fl.u. for low signals). As an additional control and validation, subsets of 10 miRs were measured by several different probe designs, which hybridize with different affinity. miR-34a showed a high expression level in the presence of active p53 and significant differential expression of above 10 fold in comparison to the non permissive temperature. Three different probe designs for miR-199a produced different absolute signal values, yet all three showed the same degree of differential expression between the two samples.

(A) Quantitative real-time RT-PCR (qRT-PCR) analysis of miR-34a expression in H1299 and H1299-TS cells cultured at the permissive (32° C.) or restrictive (37° C.) temperatures. Cells were cultured at 37° C. and then shifted to 32° C. for the indicated periods. RNA was isolated and 10 ng RNA was subjected to qRT-PCR to determine the levels of miR-34a and U6 RNA. The bars represent relative miR-34a expression, normalized to U6 in the same samples. RU—relative units.

(B) H1299 and H1299-TS cells were cultured continuously at 37° C. or transferred to 32° C. for 3 days. RNA was extracted, and 20 µg RNA was subjected to Northern blot analysis with an anti-miR34aLNA probe labeled with $^{32}$P (lower panel). Positions of size markers are shown on the right; numbers denote length in nucleotides. Small RNAs stained with ethidium bromide are shown as a loading control (upper panel).

(C) H1299 cells were transiently transfected with control (Cont) or wild type p53 expression plasmid (0.5 µg), and harvested 3 days later. Relative levels of miR-34a were determined as in (A).

(D) HCT116 cells, stably expressing either p53 shRNA (sip53) or LacZ shRNA (siLacZ), were either left untreated or treated for 16 hours with 50 µg/ml 5-FU. RNA was extracted and relative miR-34a levels were determined as in (A), except that values were normalized to 5S RNA.

(E) U2OS cells, stably expressing either p53 shRNA (sip53) or LacZ shRNA (siLacZ), were either left untreated or treated for 48 hours with 20 µM Nutlin-3. RNA was extracted and relative miR-34a levels were determined as in (A).

FIG. 3 demonstrates that miR34a is produced from a large precursor by splicing and excision of a 30 Kb intron.

(A) UCSC Genome Browser (hgl7 assembly) presentation of the location of the published spliced EST DB286351 (triangle) and pre-mIR-34a (top row, left side) on chromosome 1, strand "−". A CpG Island in proximity to the 5' end of the reported EST and p53 binding site (p53BS) are indicated; the position of the p53BS identified by us (see below) is denoted by an asterisk.

(B) Spliced sequence of the pm34a-EST. The exon-exon junction nucleotides are indicated in bold and underlined. The sequence of the miR-34a precursor (pre-miR-34a), located in the second exon, and is in italics. The sequence of the mature miR-34a is indicated in bold italics. The putative p53BS, residing within the first exon, is boxed. This putative p53BS was found by applying the p53 MH Algorithm (Hoh, 2002) to the 40 Kb sequence consisting of 35 Kb upstream and 5 Kb downstream of the mature miR-34a sequence (total length 40021 bp). The location of the putative p53BS is 30 Kb upstream to the mature miR-34a (5011 bp from the start of the examined sequence). The score of this putative p53BS was 25.85, which is the maximal score (100%) of the program. The locations of primers used for the EST cloning and for RT-PCR analysis are also indicated. Bold black arrows on the right indicate the 5' to 3' direction.

(C) cDNA prepared from the RNA of H1299-TS cells grown at 32° C. was subjected to semiquantitative PCR analysis with the primer pairs listed below each lane. The PCR products were separated by agarose gel electrophoresis. The positions of the various primers are denoted in panels (B) and (F).

Figure 3A:
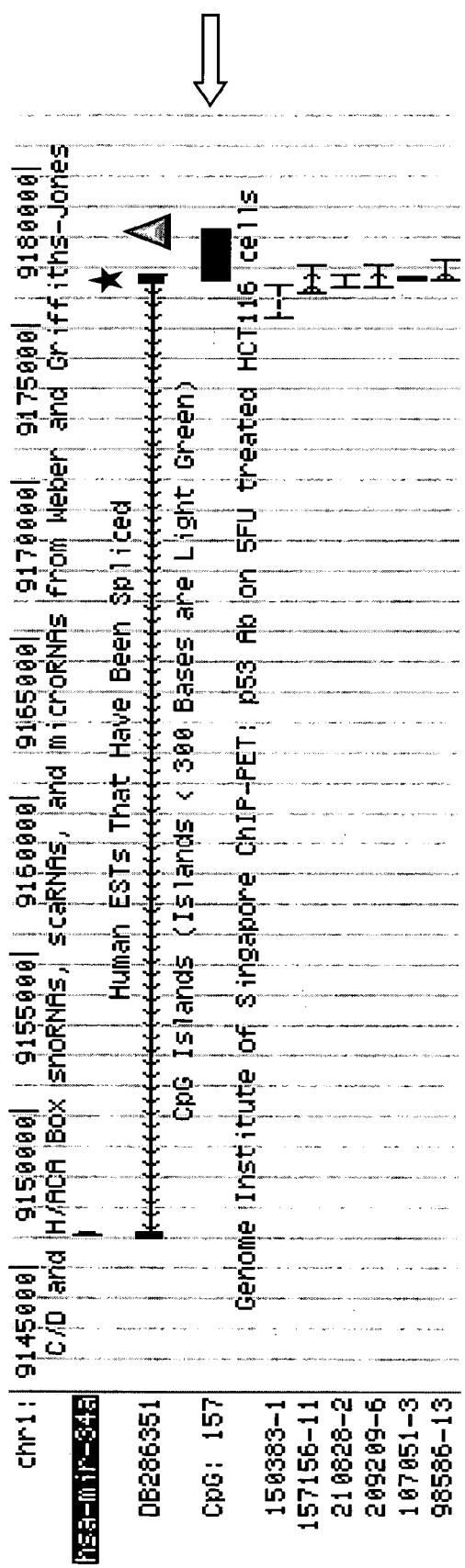
Figure 3B:
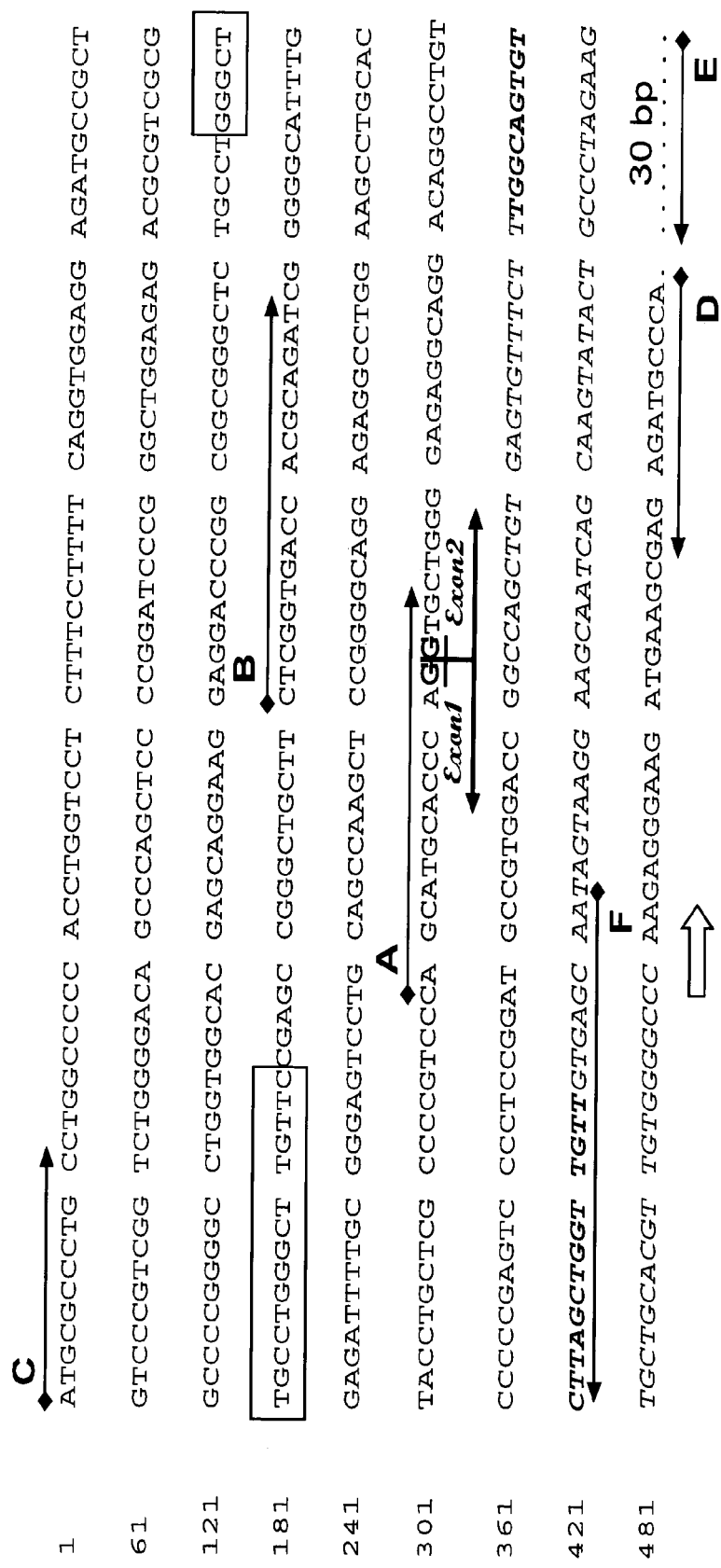

(D) H1299 cells (1299) and H1299-TS cells (TS) were incubated at the indicated temperature for either 16 hours or 3 days, and the RNA was extracted was subjected to qRT-PCR analysis with primers specific for the pm34a-EST (primers B and F, FIG. 3B). Results were normalized to HPRT expression in the same samples.

(E) RNA was extracted from the indicated cell lines, stably expressing either p53 shRNA (sip53), LacZ shRNA (siLacZ), or empty shRNA expression vector (Cont), as well as from HCT116 cells in which expression of full length wtp53 had been somatically knocked out (p53–/–) and parental, p53-proficient HCT116 cells (p53+1+). qRT-PCR was performed on cDNA derived from 100 ng RNA, employing primers E1 and E2 (FIG. 3B) to amplify the pm34a-EST. Results were normalized to HPRT expression in the same samples. RU—relative units.

(F) Schematic view of the genomic organization of the primary transcript and its processing into mature miR-34a. A-E represents the positions of primers used for RT-PCR analysis. E1 and E2 denote exon 1 and exon 2, respectively. The locations of the pri-miR34a (SEQ ID NO: 10), pre-miR34a (SEQ ID NO: 46) and mature miR-34a (SEQ ID NO: 1) are also indicated.

FIG. 4 demonstrates that the induction of pm34a-EST and miR-34a by p53 does not require de novo protein synthesis.

(A) H1299 and 111299-TS cells were either left untreated or supplemented with 80 nM cycloheximide (CHX) for 30 min before being shifted to either 37° C. or 32° C. Cells were then incubated for the indicated time periods with continuous exposure to the drug. RNA was isolated and subjected to qRT-PCR analysis with primers specific for pm34a-EST. Values were normalized for HPRT in the same samples.

(B) H1299-TS cells were processed essentially as in (A), except that CHX was added only where indicated. RNA was subjected to qRT-PCR with primers specific for mature miR-34a. Values were normalized for U6 RNA in the same samples.

(C) The same RNA samples as in (B) were subjected to qRT-PCR analysis with primers specific for p21 mRNA. Values were normalized for HPRT in the same samples.

(D) The same RNA samples as in (A) were subjected to qRT-PCR analysis with primers specific for GAPDH mRNA. Values were normalized for HPRT.

FIG. 5 demonstrates that p53 binds to the miR-34a precursor gene and activates transcription from its promoter.

(A) HCT116 cells stably expressing shRNA specific for p53 (sip53) or for LacZ (siLacZ) were either left untreated or treated for 16 hours with 50 µg/ml 5-FU, and then subjected to ChIP analysis with antibodies directed against p53 or HA as a control. The precipitated DNA was subjected to quantitative real-time PCR analysis with primers spanning the 5' p53BS of the p21 gene, the putative p53BS of the pm34a-EST, or the GAPDH gene as a negative control.

(B) Schematic representation of the DNA fragment (thick bar) cloned into the luciferase reporter plasmid. The positions of the p53BS and exons 1 and 2 of the pm34a-EST are also indicated.

(C) The putative promoter of the pm34a-EST was cloned upstream to the firefly luciferase reporter gene in the pGL3-basic vector to yield plasmid EST-Prom-luc. EST-Prom-luc was transfected into H1299 cells without or with the indicated amounts of p53 expression plasmid. Luciferase activity was then measured by the dual luciferase assay, and normalized for Renilla luciferase activity. Results are represented as fold induction relative to cells without p53. pGL3-basic served as a negative control. RGC-luc and RGC-M-luc contain 17 tandem copies of a synthetic wild type or mutated (non-p53 binding) p53BS, respectively, derived from the ribosomal gene cluster (Kern, et al., 1991), upstream to firefly luciferase.

(D) HCT116 cells were transfected with the indicated luciferase reporter plasmids, together with siRNA oligonucleotides against LacZ or p53. Where indicated, the cells were also incubated with 50 µM 5-FU for 16 hours before being harvested. Luciferase analysis was done as in (C).

FIG. 6 demonstrates that miR-34a inhibits colony formation and contributes to cell death.

(A) H1299 cells were transfected with empty pcDNA3 vector (Cont) or plasmid pcDNA3-pm34a-EST (EST). RNA was isolated 72 hours later, and 7.5 □g RNA was subjected to Northern blot analysis. Detection was performed with $^{32}$P-labeled LNA anti-miR-34a. Asterisk denotes the position of the mature miR-34a. Positions of size markers are shown on the left. Nts—nucleotides.

The upper panel shows small RNAs stained with ethidium bromide (loading control).

(B) H1299 cells were transfected with pcDNA3, pcDNA3-pm34a-EST, or pcDNA3-pm34a-EST-MUT (a derivative of pcDNA3-pm34a-EST in which mutations were introduced to abolish production of mature miR-34a). RNA was isolated 72 hours later, and subjected to qRT-PCR to determine relative levels of expression of pm34a-EST (EST, normalized to HPRT) and mature miR-34A (normalized to U6 RNA). Control vector-transfected H1299 cells (pcDNA) contain negligible levels of these RNA species, while cells transfected with pcDNA3-pm34a-EST-MUT express abundant pm34a-EST but no detectable mature miR-34a.

(C) H1299 cells were co-transfected with pcDNA3 (Cont) or with pcDNA3-pm34a-EST (EST), together with pBabe-puro plasmid DNA; where indicated, a p53 expression plasmid (1 µg) was also included. Cultures were maintained for 2 weeks with continuous puromycin (1.5 µg/ml) selection, and then fixed, stained and photographed.

(D) Quantification of the data shown in (C). Colonies were counted manually (some of the colonies are too small to be seen in (C) at this photograph size). Results are presented as average +/–SEM. The effect of EST over pcDNA is significant with a P value of 0.001, and the effect of p53 is significant with P<0.0001, as determined by 2-way ANOVA. (E) H1299 cells were transfected with either pcDNA3-pm34a-EST (EST) or pcDNA3-pm34a-EST-MUT (MUT), together with pBabe-puro plasmid DNA; where indicated, a p53 expression plasmid (1 µg) was also included. Cultures were maintained as in (C), and analysis was as in (D). Transfections were done in triplicates and results are presented as average +/−SEM.

(F) HEK293 cells were transfected with a GFP expression plasmid together with either pcDNA3, pcDNA3-pm34a-EST-MUT (MUT), or pcDNA3-pm34a-EST (EST). 72 hours later, cells were fixed, stained with propidium iodide, and subjected to FACS-based DNA content analysis; only GFP-positive cells, identified by appropriate gating in the FACS, are shown. Cultures transfected with pcDNA3-pm34a-EST exhibited an increased proportion of cells with sub-G1 DNA content, indicative of apoptosis (P<0.05; unpaired t test). A representative FACS pattern is shown above the quantitative analysis of triplicate transfections.

(G) U2OS cells stably expressing shRNA directed against p53 (sip53) or against LacZ as a control (siLacZ) were exposed to 20 µM Nutlin-3 for 48 hours where indicated, together with 100 nM anti-miR-34a LNA (34a) or scrambled miR LNA (cont). Representative microscopic fields are shown on the left. Cells were fixed, stained with propidium iodide, and subjected to FACS-based DNA content analysis (right panels). Percentages of cells with sub-G1 DNA content, indicative of apoptosis, are indicated.

FIG. 7 shows protein and RNA analysis data.
(A) Western blot analysis of 20 µg protein extracts from H1299 and H1299-TS cells incubated at the indicated temperature for 18 h.
(B) H1299 and H1299-TS cells were maintained at the indicated temperatures for 72 h. RNA was isolated and 10 ng was subjected to qRT-PCR analysis of miR-199a expression. Values were normalized to U6 RNA in the same samples. RU—relative units.
(C) H1299 and H1299-TS cells were maintained at the indicated temperatures for the indicated time periods. RNA was extracted and 1 ng of each sample was subjected to qRT-PCR analysis of p21 mRNA. Results were normalized to HPRT expression in the same samples.
(D) H1299 cells were transiently transfected with wtp53 expression plasmid as indicated. 72 h later, total RNA was extracted and subjected to qRT-PCR analysis of p21 mRNA and p53 mRNA. Results were normalized to HPRT expression in the same samples.

FIG. 8 shows miRs expression profiling of H1299 and H1299-TS cells.
(A) Comparative analysis of the miRdicator™ array hybridization data of Cy5 probes prepared from the RNA of H1299 cells cultured at 32° C. versus H1299 cells cultured at 37° C., (hybridized in parallel with the Cy3H1299-TS probes; see FIG. 1 for details). Data is presented in arbitrary fluorescence units (fl.u.). Blue crosses represent signals for all human miRs, magenta squares represent background and non-specific probes, green circles represent signals of synthetic spike-in controls, and red diamonds indicate human miRs displaying notable differential expression. Each miR probe was spotted in triplicate and each data point in the figure represents at least 2 spots that fall within ±14% of the value indicated (or ±100 fl.u. for low signals), and none being further off than ±73% of this value (or ±300 fl.u. for low signals). No meaningful temperature effect on the expression of specific miRs could be observed. (B) Comparative analysis of the miRdicator™ array data obtained with RNA extracted from H1299-TS cells (conjugated to Cy3) and H1299 cells (conjugated to Cy5), both cultured at 37° C., and hybridized overnight to the same array; the H1299-TS data is the same as in FIG. 1, and the H1299 data is the same as in FIG. 12A. The analysis reveals that different probes for miR-199a detect overexpression of that miR in 111299-TS cells at the non-permissive temperature, suggesting that miR-199a is positively regulated by mutant p53.

FIG. 9 shows validation of shRNA-mediated p53 inactivation in HCT116 and U2OS cells.
(A) HCT116 cells stably expressing shRNA against p53 (sip53) or LacZ (siLacZ) were either treated with 50 µg/ml 5-FU for 16 h or left untreated. 1 ng total RNA from each sample was subjected to qRT-PCR analysis of p21 mRNA. Results were normalized to HPRT expression in the same samples.
(B) U2OS cells stably expressing shRNA against p53 (sip53) or LacZ (siLacZ) were either treated with 20 µM Nutlin-3 for 48 h or left untreated. RNA from each sample was subjected to qRT-PCR analysis of p53 mRNA and p21 mRNA. Results were normalized to HPRT expression in the same samples. p21 mRNA was increased 10.3 fold upon Nutlin treatment. The modest increase in p53 mRNA (1.8 fold) has not been further investigated.
(C) Western blot analysis of 20 µg total protein extracted from parallel cultures treated as in (A).
(D) Western blot analysis of 20 µg total protein extracted from parallel cultures treated as in (C).

Figure 10:
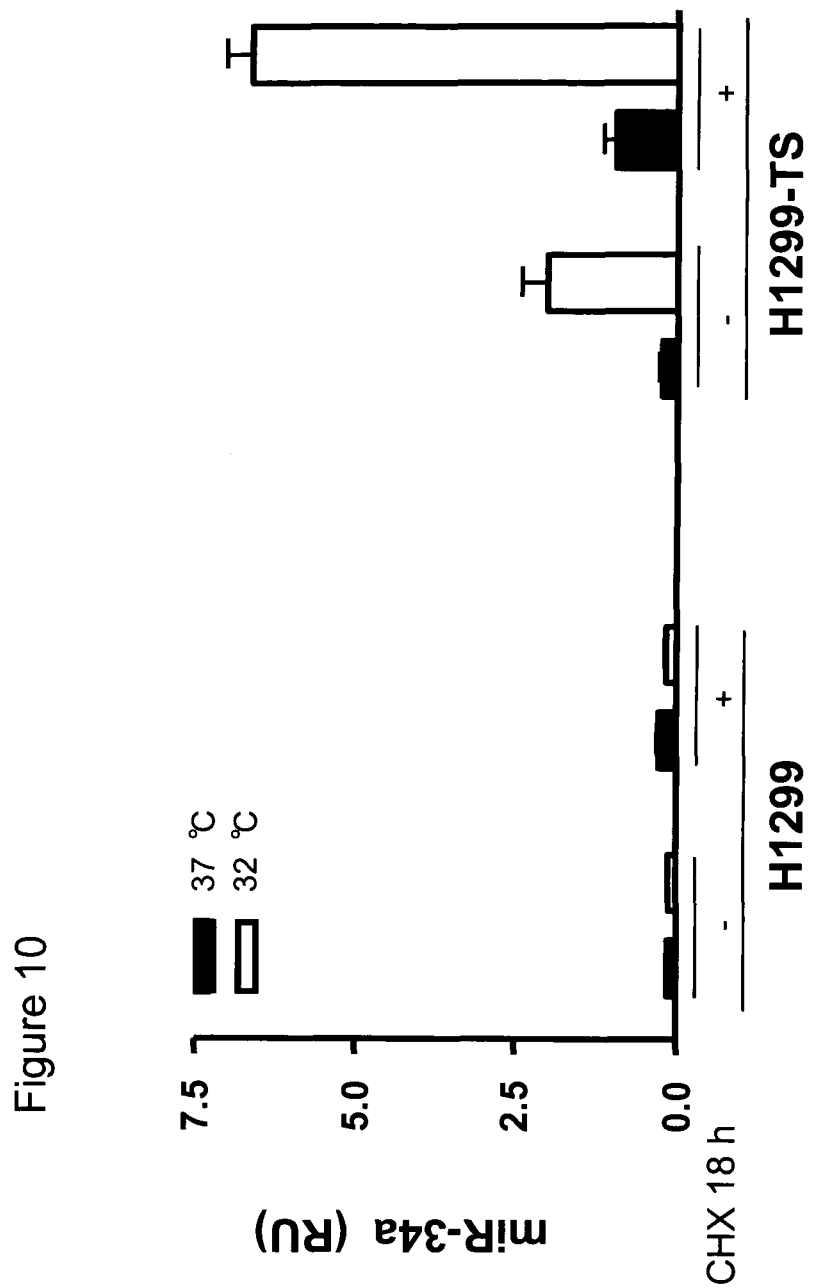

FIG. 10 demonstrates that cycloheximide does not prevent the induction of miR-34a by p53.
H1299 and H1299-TS cells were treated with 80 nM cycloheximide (CHX) for 30 min at 37° C. and then shifted to 32° C. or maintained at 37° C. for an additional 18 h, in continuous presence of the drug. RNA was isolated and subjected to qRT-PCR analysis of miR-34a expression. Values were normalized to U6 RNA. RU—relative units.

Figure 11:
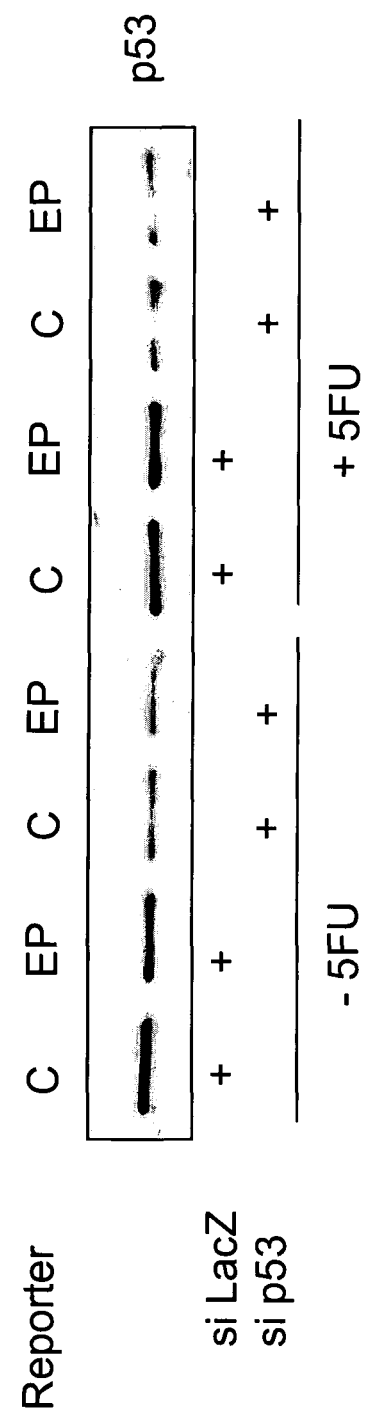

FIG. 11 demonstrates validation of p53 knockdown in samples used for luciferase assay.
Protein extracts of the cells employed for luciferase analysis in FIG. 5D were subjected to SDS-PAGE followed by Western blot analysis for p53. GAPDH protein served as a loading control. C— cells transfected with pGL3-basic empty vector; EP—cells transfected with EST-Prom-luc. See FIG. 5 for further details.

FIG. 12 illustrates putative ORF from miR-34a locus and production of mature miR-34a by transfected expression plasmid.
(A) Putative ORF in pm34a-EST. Asterisk denotes the translational stop codon, underlined letters indicate positions of mutations introduced into pcDNA3-pm34a-EST in order to generate pcDNA3-pm34a-EST-MUT, which can not give rise to mature miR-34a. The miR-34a sequence is in bold, and the miR-34a precursor sequence is in italics.
(B) Transfected pcDNA3-pm34a-EST, but not pcDNA3-pm34a-EST-MUT, gives rise to mature miR-34a in HEK-293 cells. HEK-293 cells were transfected with empty pcDNA3 vector, pcDNA3-pm34a-EST-MUT (MUT) or pcDNA3-pm34a-EST (EST). RNA was isolated 72 hours later, and 15 µg RNA was subjected to Northern blot analysis. Detection was performed with $^{32}$P-labeled LNA anti-miR-34a. Positions of size markers are shown on the left. Nts—nucleotides.

FIG. 13 demonstrates that miR-34a regulates the Notch pathway activity.
(A) Predicted binding sites for miR-34a in 3' UTR of Jag1.
(B) A172 cells were transfected with either scrambled or anti-miR-34a LNA oligos. RNA was isolated 72 hours later, and subjected to qRT-PCR to determine relative levels of expression of DLL1, Jag1 and Notch1 (normalized to GAPDH).
(C) A172 cells were transfected with pcDNA3-pm34a-EST-MUT (MUT) or pcDNA3-pm34a-EST (EST). RNA extraction and analysis was as in (B).

(D) MCF7 cells were transfected with scramble or anti-miR-34a LNA oligos. 24 h post-transfection, 20 μM Nutlin-3 was added to the half of the samples for additional 48 h. RNA extraction and analysis was as in (B).

(E) MCF7 cells were transfected with pcDNA3-pm34a-EST-MUT (MUT) or pcDNA3-pm34a-EST (EST) with (filled bars) or without (empty bars) addition of constitutively active intracellular part of Notch1 expression plasmid. 72 h later the cells were fixed and stained with PI and subjected to the FACS analysis. The results represent fold induction relatively to the subG1 population of cells transfected with pcDNA3-pm34a-EST-MUT. Absolute numbers of subG1 were: pcDNA3-pm34a-EST-MUT—3.6%, pcDNA3-pm34a-EST-MUT+Notch1-5%, pcDNA3-pm34a-EST—9%, pcDNA3-pm34a-EST with Notch1-5.6%.

FIG. 14 demonstrates that ectopically expressed miR-34a reduces Bcl-2 protein. (A) H1299 or U2OS cells were transiently transfected with 100 nM control scrambled RNA (cont) or pre-miR-34a RNA oligonucleotides (pre-34a, Ambion) using siPORT NeoFX transfection reagent (Ambion). Three days post-transfection, cell extracts were prepared. 30 μg of total protein was subjected to SDS-15% polyacrylamide gel electrophoresis followed by Western blot analysis with antibodies directed against GAPDH (MAB374, Chemicon) and Bcl-2 (C-2, Santa Cruz). (B) Total RNA was extracted from identical cultures as in (A) using the mirVana miRNA isolation kit (Ambion). RNA was converted to cDNA using random hexamers and MMLV reverse transcriptase (Promega). cDNA obtained from 10 ng total RNA was subjected to real-time PCR analysis using specific primers for Bcl-2 mRNA (forward primer—5'-CTGGGATGC-CTTTGTGGAAC-3' (SEQ ID NO: 42), reverse primer—5'-ATCAAACAGAGGCCGCATG-3' (SEQ ID NO: 43) and super SYBR-green ready mix (Applied Biosystems) in an ABI PRISM 7300 Sequence Detection System (Applied Biosystems). Bcl-2 mRNA levels were normalized relative to GAPDH mRNA (forward primer—5'-GTCGGAGT-CAACGGATTTGG-3' (SEQ ID NO: 44), reverse primer—5'-AAAAGCAGCCCTGGTGACC-3') (SEQ ID NO: 45) in the same samples. RU=relative units. (C) 200 ng of total RNA obtained from (B) was subjected to quantitative real-time RT-PCR using primers for mature miR-34a. Values were normalized relative to U6 RNA levels in the same samples.

DETAILED DESCRIPTION OF THE INVENTION

According to the present invention, p53 can induce the expression of miR-34a (SEQ ID NO: 1), by binding to a perfect p53 binding site located within the gene that gives rise to miR-34a. Overexpression of miR-34a exerts antiproliferative effects and promotes cell death, whereas inactivation of miR-34a attenuates p53-mediated cell death. Hence, miR-34a is a direct transcriptional target of p53, which may mediate some of the biological effects of this tumor suppressor. Perturbation of miR-34a expression may thus contribute to tumorigenesis.

Expression of miR-34a is augmented by p53 in response to pertinent stress signals, as demonstrated here for the anticancer drug 5-FU. Furthermore, excessive levels of miR-34a exert inhibitory antiproliferative effects and promote cell death, whereas endogenous miR-34a can contribute to p53-dependent cell death.

The compositions of the invention or their modulators may be administered to a subject to prevent or treat a disorder or disease associated with the p53 gene, including but not limited to cancer, neurodegenerative diseases which are associated with increased cell death including Alzheimers', Parkinsons', and infectious disease.

DEFINITIONS

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

Aberrant Proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of cell death, or both. Such indications may be characterized, for example, by single or multiple local abnormal proliferations of cells, groups of cells, or tissue(s), whether cancerous or non-cancerous, benign or malignant.

About

As used herein, the term "about" refers to +/−10%.

Acceptable Safety Profile

"Acceptable safety profile" means a pattern of side effects that is within clinically acceptable limits.

Administering

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Chemoembolization" means a procedure in which the blood supply to a tumor is blocked surgically or mechanically and chemotherapeutic agents are administered directly into the tumor.

Amelioration

The term "amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

Apoptosis

"Apoptosis" as used herein, refers to a form of cell death that includes progressive contraction of cell volume with the preservation of the integrity of cytoplasmic organelles; condensation of chromatin (i.e., nuclear condensation), as viewed by light or electron microscopy; and/or DNA cleavage into nucleosome-sized fragments, as determined by centrifuged sedimentation assays. Apoptosis occurs when the membrane integrity of the cell is lost (e.g., membrane blebbing) with engulfment of intact cell fragments ("apoptotic bodies") by phagocytic cells.

Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein may mean a sample of biological tissue or fluid that comprises nucleic acids. Such samples include, but are not limited to, tissue or fluid isolated from animals. Biological samples may also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from animal or patient tissues. Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, non-small cell lung, oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Cell Death

"Cell death" as used herein refers to cell-death by an accidental (necrosis) manner, which is a form of cell-death that results from acute tissue injury and provokes an inflammatory response, cell-death by a programmed pathway (programmed cell-death) or cell-death by autophagy.

"Programmed cell-death (PCD)" as used herein means death of a cell in any form, mediated by an intracellular program. PCD is carried out in a regulated process which generally confers advantage during an organism's life-cycle. PCD serves fundamental functions during both plant and metazoa (multicellular animals) tissue development. Three types of PCD are characterized: (i) Apoptosis or Type I cell-death; (ii) Autophagic or Type II cell-death; (iii) "non-apoptotic programmed cell-death" (or "caspase-independent programmed cell-death" or "necrosis-like programmed cell-death") which is an alternative route to death are as efficient as apoptosis and can function as either backup mechanisms or the main type of PCD.

"Necrosis" as used herein means accidental death of cells and living tissue. Necrosis is less orderly than apoptosis. The disorderly death generally does not send cell signals which tell nearby phagocytes to engulf the dying cell. This lack of signaling makes it harder for the immune system to locate and recycle dead cells which have died through necrosis than if the cell had undergone cell death. The release of intracellular content after cellular membrane damage is the cause of inflammation in necrosis.

"Autophagy" as used herein means a catabolic process involving the degradation of a cell's own components through the lysosomal machinery. It is a tightly regulated process which plays a normal part in cell growth, development, and homeostasis, where it helps maintain a balance between the synthesis, degradation, and subsequent recycling of cellular products. It is a major mechanism by which a starving cell reallocates nutrients from unnecessary processes to more essential processes. A variety of autophagic processes exist, all sharing in common the degradation of intracellular components via the lysosome. The most well known mechanism of autophagy involves the formation of a membrane around a targeted region of the cell, separating the contents from the rest of the cytoplasm. The resultant vesicle then fuses with a lysosome and subsequently degrades the contents.

Chemotherapy

"Chemotherapy" as used herein means treatment of a subject with one or more pharmaceutical agents that kills cancer cells and/or slows the growth of cancer cells.

Complement

"Complement" or "complementary" as used herein refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

Dose

"Dose" as used herein means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

Dosage Unit

"Dosage unit" as used herein means a form in which a pharmaceutical agent is provided. In certain embodiments, a dosage unit is a vial containing lyophilized oligonucleotide. In certain embodiments, a dosage unit is a vial containing reconstituted oligonucleotide.

Duration

"Duration" as used herein means the period of time during which an activity or event continues. In certain embodiments, the duration of treatment is the period of time during which doses of a pharmaceutical agent or pharmaceutical composition are administered.

Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Host Cell

"Host cell" used herein may be a naturally occurring cell or a transformed cell that may contain a vector and may support replication of the vector. Host cells may be cultured cells, explants, cells in vivo, and the like. Host cells may be prokaryotic cells such as *E. coli*, or eukaryotic cells such as yeast, insect, amphibian, or mammalian cells, such as CHO and HeLa.

Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

Inhibit

"Inhibit" as used herein may mean prevent, suppress, repress, reduce or eliminate.

Label

"Label" as used herein may mean a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Metastasis

"Metastasis" as used herein means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

Mismatch

"Mismatch" as used herein means a nucleobase of a first nucleic acid that is not capable of pairing with a nucleobase at a corresponding position of a second nucleic acid.

Modulation

"Modulation" as used herein refers to up regulation or down regulation of cell death or cell proliferation.

Modified Oligonucleotide

"Modified oligonucleotide" as used herein means an oligonucleotide having one or more modifications relative to a naturally occurring terminus, sugar, nucleobase, and/or internucleoside linkage. According to one embodiment, the modified oligonucleotide is a miRNA comprising a modification (e.g. labeled).

Mutant

"Mutant" as used herein refers to a sequence in which at least a portion of the functionality of the sequence has been lost, for example, changes to the sequence in a promoter or enhancer region will affect at least partially the expression of a coding sequence in an organism. As used herein, the term "mutation," refers to any change in a sequence in a nucleic acid sequence that may arise such as from a deletion, addition, substitution, or rearrangement. The mutation may also affect one or more steps that the sequence is involved in. For example, a change in a DNA sequence may lead to the synthesis of an altered mRNA and/or a protein that is active, partially active or inactive.

Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Operably Linked

"Operably linked" used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

Overall Survival Time

"Overall survival time" as used herein means the time period for which a subject survives after diagnosis of or treatment for a disease. In certain embodiments, the disease is cancer.

Probe

"Probe" as used herein may mean an oligonucleotide capable of binding to a target nucleic acid of complementary sequence through one or more types of chemical bonds, usually through complementary base pairing, usually through hydrogen bond formation. According to one embodiment, the probe comprises a sequence which is complementary to that of SEQ ID NOS: 10-11, 38-41.

Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Progression-Free Survival

"Progression-free survival" means the time period for which a subject having a disease survives, without the disease getting worse. In certain embodiments, progression-free survival is assessed by staging or scoring the disease. In certain embodiments, progression-free survival of a subject having cancer is assessed by evaluating tumor size, tumor number, and/or metastasis.

Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

Reduced Tumorigenicity

"Reduced tumorigenicity" as used herein refers to the conversion of hyperproliferative (e.g., neoplastic) cells to a less proliferative state. In the case of tumor cells, "reduced tumorigenicity" is intended to mean tumor cells that have become less tumorigenic or non-tumorigenic or non-tumor cells whose ability to convert into tumor cells is reduced or eliminated. Cells with reduced tumorigenicity either form no tumors in vivo or have an extended lag time of weeks to months before the appearance of in vivo tumor growth. Cells with reduced tumorigenicity may also result in slower growing three dimensional tumor mass compared to the same type of cells having fully inactivated or non-functional tumor suppressor gene growing in the same physiological milieu (e.g., tissue, organism age, organism sex, time in menstrual cycle, etc.).

Selectable Marker

"Selectable marker" used herein may mean any gene which confers a phenotype on a host cell in which it is expressed to facilitate the identification and/or selection of cells which are transfected or transformed with a genetic construct. Representative examples of selectable markers include the ampicillin-resistance gene (Amp$^r$), tetracycline-resistance gene (Tc$^r$), bacterial kanamycin-resistance gene (Kan$^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein (GFP)-encoding gene and luciferase gene.

Senescence

"Senescence" used herein may include permanent cessation of DNA replication and cell growth not reversible by growth factors, such as occurs at the end of the proliferative life span of normal cells or in normal or tumor cells in response to cytotoxic drugs, DNA damage or other cellular insult. Senescence is also characterized by certain morphological features, including increased size, flattened morphology increased granularity, Side Effect "Side effect" as used herein means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" used herein may mean that a first sequence is at least 60%-99% identical to the complement of a second sequence over a region of 8-50 or more nucleotides, or that the two sequences hybridize under stringent hybridization conditions.

Substantially Identical

Substantially identical" used herein may mean that a first and second sequence are at least 60%-99% identical over a region of 8-50 or more nucleotides or amino acids, or with respect to nucleic acids, if the first sequence is substantially complementary to the complement of the second sequence.

Subject

"Subject" as used herein refers to a mammal, including both human and other mammals. The methods of the present invention are preferably applied to human subjects.

Target

"Target" as used herein may mean a polynucleotide that may be bound by one or more probes under stringent hybridization conditions.

Therapeutically Effective Amount

"Therapeutically effective amount" or "therapeutically efficient" used herein as to a drug dosage, refer to dosage that provides the specific pharmacological response for which the drug is administered in a significant number of subjects in need of such treatment. The "therapeutically effective amount" may vary according, for example, the physical condition of the patient, the age of the patient and the severity of the disease.

Therapy

"Therapy" as used herein means a disease treatment method. In certain embodiments, therapy includes, but is not limited to, chemotherapy, surgical resection, transplant, and/or chemoembolization.

Treat

"Treat" or "treating" used herein when referring to protection of a subject from a condition may mean preventing, suppressing, repressing, or eliminating the condition. Preventing the condition involves administering a composition described herein to a subject prior to onset of the condition. Suppressing the condition involves administering the composition to a subject after induction of the condition but before its clinical appearance. Repressing the condition involves administering the composition to a subject after clinical appearance of the condition such that the condition is reduced or prevented from worsening. Elimination of the condition involves administering the composition to a subject after clinical appearance of the condition such that the subject no longer suffers from the condition.

Unit Dosage Form

"Unit dosage form," used herein may refer to a physically discrete unit suitable as a unitary dosage for a human or animal subject. Each unit may contain a predetermined quantity of a composition described herein, calculated in an amount sufficient to produce a desired effect in association with a pharmaceutically acceptable diluent, carrier or vehicle. The specifications for a unit dosage form may depend on the particular composition employed and the effect to be achieved, and the pharmacodynamics associated with the composition in the host.

Variant

"Variant" used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Vector

"Vector" used herein may mean a nucleic acid sequence containing an origin of replication. A vector may be a plasmid, bacteriophage, and bacterial artificial chromosome or yeast artificial chromosome. A vector may be a DNA or RNA vector. A vector may be either a self-replicating extrachromosomal vector or a vector which integrates into a host genome.

Wild Type

As used herein, the term "wild type" sequence refers to a coding, non-coding or interface sequence is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

MicroRNA

A gene coding for a miRNA may be transcribed leading to production of a miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 30-200 nt precursor known as the pre-miRNA. Drosha may cleave the pri-miRNA with a staggered cut typical of RNase III endonucleases yielding a pre-miRNA stem loop with a 5' phosphate and ±2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specifity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 Genes Dev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet. 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

MiRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acid

Nucleic acids are provided herein. The nucleic acid may comprise the sequence of SEQ ID NOS: 1-54 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 530 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200, 250 or 530 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

Nucleic Acid Complex

The nucleic acid may further comprise one or more of the following: a peptide, a protein, a RNA-DNA hybrid, an antibody, an antibody fragment, a Fab fragment, and an aptamer. The nucleic acid may also comprise a protamine-antibody fusion protein as described in Song et al (Nature Biotechnology 2005; 23:709-17) and Rossi (Nature Biotechnology 2005:23; 682-4), the contents of which are incorporated herein by reference. The protamine-fusion protein may comprise the abundant and highly basic cellular protein protamine. The protamine may readily interact with the nucleic acid. The protamine may comprise the entire 51 amino acid protamine peptide or a fragment thereof. The protamine may be covalently attached to another protein, which may be a Fab. The Fab may bind to a receptor expressed on a cell surface.

Pri-miRNA

The nucleic acid may comprise a sequence of a pri-miRNA or a variant thereof. The pri-miRNA sequence may comprise from 45-30,000, 50-25,000,100-20,000, 1,000-1,500, 500-750, or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-11, 46-54 or variants thereof.

The pri-miRNA may form a hairpin structure. The hairpin may comprise first and second nucleic acid sequences that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-200, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-9, 46-54 or variants thereof.

MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-9 or variants thereof.

Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g. antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complimentary to the 5' of a miRNA and at least 5-12 nucleotides that are substantially complimentary to the flanking regions of the target site from the 5' end of the miRNA, or (b) at least 5-12 nucleotides that are substantially identical or complimentary to the 3' of a miRNA and at least 5 nucleotide that are substantially complimentary to the flanking region of the target site from the 3' end of the miRNA. The sequence of the anti-miRNA may comprise the compliment of SEQ ID NOS: 1-54 or variants thereof.

Binding Site of Target

The nucleic acid may also comprise a sequence of a target microRNA binding site, or a variant thereof. The target site sequence may comprise a total of 5-100 or 10-60 nucleotides. The target site sequence may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62 or 63 nucleotides. The target site sequence may comprise at least 5 nucleotides of the sequence of SEQ ID NOS: 1-54. According to one embodiment, the target site sequence is set forth in SEQ ID NOS: 11, 38-41.

Synthetic Gene

A synthetic gene is also provided comprising a nucleic acid described herein operably linked to a transcriptional and/or translational regulatory sequence. The synthetic gene may be capable of modifying the expression of a target gene with a binding site for a nucleic acid described herein. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

Vector

A vector is also provided comprising a synthetic gene described herein. The vector may be an expression vector. An expression vector may comprise additional elements. For example, the expression vector may have two replication systems allowing it to be maintained in two organisms, e.g., in one host cell for expression and in a second host cell (e.g., bacteria) for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

Host Cell

A host cell is also provided comprising a vector, synthetic gene or nucleic acid described herein. The cell may be a bacterial, fungal, plant, insect or animal cell. For example, the host cell line may be DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines may be available from commercial services, the American Tissue Culture Collection or from published literature.

Probes

A probe is also provided comprising a nucleic acid described herein. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated With streptavidin, resulting in attachment. Alternatively, probes may be synthesized on the surface using techniques such as photopolymerization and photolithography.

Compositions

A pharmaceutical composition is also provided. The composition may comprise a nucleic acid described herein and optionally a pharmaceutically acceptable carrier. The composition may encompass modified oligonucleotides that are identical, substantially identical, substantially complementary or complementary to any nucleobase sequence version of the miRNAs described herein or a precursor thereof.

In certain embodiments, a nucleobase sequence of a modified oligonucleotide is fully identical or complementary to a miRNA nucleobase sequence listed herein, or a precursor thereof. In certain embodiments, a modified oligonucleotide has a nucleobase sequence having one mismatch with respect to the nucleobase sequence of the mature miRNA, or a precursor thereof. In certain embodiments, a modified oligonucleotide has a nucleobase sequence having two mismatches with respect to the nucleobase sequence of the miRNA, or a precursor thereof. In certain such embodiments, a modified oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, a modified oligonucleotide consists of a number of linked nucleosides that is equal to the length of the mature miRNA.

In certain embodiments, the number of linked nucleosides of a modified oligonucleotide is less than the length of the mature miRNA. In certain such embodiments, the number of linked nucleosides of a modified oligonucleotide is one less than the length of the mature miRNA. In certain such embodiments, a modified oligonucleotide has one less nucleoside at the 5' terminus. In certain such embodiments, a modified oligonucleotide has one less nucleoside at the 3' terminus. In certain such embodiments, a modified oligonucleotide has two fewer nucleosides at the 5' terminus. In certain such embodiments, a modified oligonucleotide has two fewer nucleosides at the 3' terminus. A modified oligonucleotide having a number of linked nucleosides that is less than the length of the miRNA, wherein each nucleobase of a modified oligonucleotide is complementary to each nucleobase at a corresponding position in a miRNA, is considered to be a modified oligonucleotide having a nucleobase sequence that is fully complementary to a portion of a miRNA sequence.

In certain embodiments, a modified oligonucleotide consists of 15 to 30 linked nucleosides. In certain embodiments, a modified oligonucleotide consists of 19 to 24 linked nucleosides. In certain embodiments, a modified oligonucleotide consists of 21 to 24 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides. In certain embodiments, a modified oligonucleotide consists of 26 linked nucleosides. In certain embodiments, a modified oligonucleotide consists of 27 linked nucleosides. In certain embodiments, a modified oligonucleotide consists of 28 linked nucleosides. In certain embodiments, a modified oligonucleotide consists of 29 linked nucleosides. In certain embodiments, a modified oligonucleotide consists of 30 linked nucleosides.

Modified oligonucleotides of the present invention may comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide of the present invention comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose. In certain embodiments, 2'-O-methyl group is present in the sugar residue.

The modified oligonucleotides designed according to the teachings of the present invention can be generated according to any oligonucleotide synthesis method known in the art, including both enzymatic syntheses or solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," VVolumes John Wiley & Sons, Baltimore, Md.; Perbal, B. (1988), "A Practical. Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC. It will be appreciated that an oligonucleotide comprising an RNA molecule can be also generated using an expression vector as is further described hereinbelow.

The compositions may be used for therapeutic applications. The pharmaceutical composition may be administered by known methods, including wherein a nucleic acid is introduced into a desired target cell in vitro or in vivo.

Methods for the delivery of nucleic acid molecules are described in Akhtar et al., (Trends Cell Bio. 2, 139, 1992). WO 94/02595 describes general methods for delivery of RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819.

The nucleic acids can be introduced into tissues or host cells by any number of routes, including viral infection, microinjection, or fusion of vesicles. Jet injection may also be used for intra-muscular administration, as described by Furth et al. (Anal Biochem 115 205:365-368, 1992). The nucleic acids can be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

The compositions of the present invention can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc.

In certain embodiments, a pharmaceutical composition of the present invention is administered in the form of a dosage unit (e.g., tablet, capsule, bolus, etc.). In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of a modified oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds comprising modified oligonucleotides with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition of the present invention comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides of the present invention are formulated as a prodrug. In certain embodiments, upon in vivo administration, a prodrug is chemically converted to the biologically, pharmaceutically or therapeutically more active form of a modified oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Therapeutic

A method for treating a disease or disorder associated with the p53 gene, in vivo or ex vivo is also provided. Furthermore, existing miRNA molecules may be used as starting materials for the manufacture of sequence-modified miRNA molecules. Further, miRNA molecules may be modified, in order that they are processed and then generated as double-stranded siRNAs which are again directed against therapeutically relevant targets.

As previously discussed the methods, compositions and articles of manufacture of the present invention are particularly useful in the treatment of cancer, neurodegenerative disorder and infectious disease.

The compositions of the present invention may be combined with a chemotherapeutic agent, a combination of chemotherapeutic agents and/or radiotherapy.

Cancer treatments often comprise more than one therapy. As such, in certain embodiments the present invention provides methods for treating cancer comprising administering to a subject in need thereof the composition of the present invention, and further comprising administering at least one additional therapy.

In certain embodiments, an additional therapy may also be designed to treat cancer. An additional therapy may be a chemotherapeutic agent. Suitable chemotherapeutic agents include 5-fluorouracil, gemcitabine, doxorubicine, mitomycin c, sorafenib, etoposide, carboplatin, epirubicin, irinotecan and oxaliplatin. An additional therapy may be surgical resection of tumor(s), or chemoembolization.

Diagnostic

A method of diagnosis is also provided. The method comprises detecting a differential expression level of a disease-associated nucleic acid in a biological sample. The sample may be derived from a patient. Diagnosis of a disease state in a patient may allow for prognosis and selection of therapeutic strategy. Further, the developmental stage of cells may be classified by determining temporarily expressed disease-associated nucleic acids.

In situ hybridization of labeled probes to tissue arrays may be performed. When comparing the fingerprints between an individual and a standard, the skilled artisan can make a diagnosis, a prognosis, or a prediction based on the findings. It is further understood that the nucleic acids which indicate the diagnosis may differ from those which indicate the prognosis and molecular profiling of the condition of the cells may lead to distinctions between responsive or refractory conditions or may be predictive of outcomes.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be a kit for the amplification, detection, identification or quantification of a target nucleic acid sequence. The kit may comprise a poly(T) primer, a forward primer, a reverse primer, and a probe.

The following examples are presented in order to more fully illustrate some embodiments of the invention. They should, in no way be construed, however, as limiting the broad scope of the invention.

EXAMPLES

Example 1

Experimental Procedures

1. Reagents, Cell Culture and Antibodies

5-FU and etoposide were obtained from IBCA, Nutlin-3 was purchased from Alexis, Giemsa stain was from Fluka, and G418, puromycin and cycloheximide were purchased from Sigma.

H1299 and 111299-TS human non-small lung cancer cells were cultured in RPMI-1640 (Gibco BRL) supplemented with 10% heat-inactivated fetal bovine serum (FBS, Sigma) and 1% penicillin-streptomycin (Biological Industries, Israel). The medium of H1299-TS cells was supplemented with 400 ng/ml G418. HCT116, HCT116 p53$^{-/-}$, HCT116 siLacZ and HCT116 sip53 cells were grown in McCoy's medium (Sigma) supplemented with 10% FBS, 2 mM L-glutamine (Biological Industries, Israel) and 1% penicillin-streptomycin. The last two cell lines were produced by infecting HCT116 cells with pRetroSuper-puro-sip53 or pRetro-Super-puro-siLacZ, respectively, kindly provided by Dr. R. Agami (Amsterdam, the Netherlands), followed by selection in the presence of 2 µg/ml puromycin. U2OS human osteosarcoma cells stably expressing shRNA specific for either LacZ or p53, HEK293 cells and MCF7 human breast cancer cells, stably transfected with shRNA against p53 or with empty vector (cont) were cultured in Dulbecco's modified Eagle's medium (DMEM; Gibco BRL) supplemented with 10% FBS and 1% penicillin-streptomycin. All cell lines were incubated at 37° C. in a 5% $CO_2$ atmosphere. Polyclonal antibodies against human (CM1) and mouse (CM5) p53 were from Novacostra. Polyclonal antibodies against p21 (C-19) and HA (Y-11) were obtained Santa Cruz. Monoclonal anti- GAPDH (MAB374) was from Chemicon International. Monoclonal antibodies against p53 (D01, 1801) and Hdm2 (2A9, 2A10, 4B2 and 4B11) were produced from hybridomas.

2. Plasmids, LNA Oligonucleotides and Transfections

The expression plasmid for miR-34a (pcDNA-pm34a-EST) was constructed by PCR cloning of pm34a-EST cDNA from the RNA of H1299-TS cells grown at 32° C. for 3 days. The primers used for this purpose are listed in Table 1. The PCR product was digested with HinDIII and XhoI and ligated into pcDNA3 DNA (Invitrogen) pre-digested with the same enzymes. The control mutated EST plasmid (pcDNA3-pm34a-EST-MUT) was generated using a site-directed mutagenesis kit (Promega) with the primers listed in Table 1. A firefly luciferase reporter plasmid with the miR-34a putative promoter (EST-Prom-Luc) was produced by inserting a ~2 Kb genomic region overlapping the p53BS, amplified by PCR from H1299 genomic DNA with the primers listed in Table 1, into pGL3-basic vector (Promega) digested with XhoI/HinDIII. All constructs were validated by sequencing. Anti-miR-34a or scrambled miR locked nucleic acid (LNA) oligonucleotides were obtained from Exiqon (Denmark).

For DNA transfection, H1299, HCT116 and U2OS cells were transfected with JetPEI (PolyPlus Transfection) according to the manufacturer's protocol. HEK293 were transfected by the calcium phosphate coprecipitation method. For cotransfection of oligonucleotides and DNA, HCT116 cells were transfected with siRNA for p53 or LacZ (Invitrogen) at a final concentration of 80 nM together with the plasmids of interest, using Dharmafect reagent #1 (Dharmacon). For LNA oligonucleotide transfection, U2OS cells were transfected with anti-miR-34a or control scrambled miR LNA oligonucleotides at a final concentration of 100 nM, using the siPORT NeoFX reagent (Ambion) according to the manufacturer's instructions.

TABLE 1 miR-34a related primers that were used in the invention

| Name | Sequence | Position* | Purpose | SEQ ID NO: |
|---|---|---|---|---|
| C | 5'-tttaagcttATGCG CCCTGCC-3' | 1 | EST cloning | 12 |
| B | 5'-CTCGGTGACCAC GCAGATC-3' | 211 | Expression RT-PCR | 13 |
| A | 5'-CAGCATGCACCCA GGTG-3' | 319 | Expression RT-PCR | 14 |
| F | 5'-TTGCTCACAACAAC CAGCTAAGA-3' | 442 | Expression RT-PCR | 15 |
| D | 5'-tttctcgagTGGGC ATCTCTCG-3' | 529 | Expression 16 | 16 |
| E | 5'-tttctcgagAGAGCT TCCGAAGTCCTGG-3' | 563 | EST cloning | 17 |
| Pr-F | 5'-tttctcgagCACCTGG GTAGCATTCGCTTCC-3' | -1472 | Promoter cloning | 18 |
| Pr-R* | 5'-tttaagcttCGCG CGTTCACCTCG-3' | Exon 1 +551 | Promoter cloning | 19 |
| Mut-F | 5'-AGTGTTTCTTCCGGA GAGTCTTAGCTG-3' | 416 | miR-34a mutation | 20 |

TABLE 1-continued miR-34a related primers that were used in the invention

| Name | Sequence | Position* | Purpose | SEQ ID NO: |
|---|---|---|---|---|
| Mut-R | 5'-CAGCTAAGACTCTCC GGAAGAAACACT-3' | 428 | miR-34a mutation | 21 |
| 34-RE-F* | 5'-ACGCTTGTGTTTCT CAGTCCG-3' | Exon 1 +5 | ChIP RT-PCR | 22 |
| 34-RE-R* | 5'-TGGTCTAGTTCCC GCCTCCT-3' | Exon 1 +73 | ChIP RT-PCR | 23 |

*the primers are located in the intron between exon 1 and exon 2
**letters in the lowercase represent non-relevant ends and restriction sites for cloning purposes
***relatively to the spliced EST

TABLE 2

Control primers that were used in the invention

| Name | Sequence | Purpose | SEQ ID NO: |
|---|---|---|---|
| p21-F | 5'-GGAGACAGGAGAC CTCTAAAG-3' | ChIP RT-PCR | 24 |
| p21-R | 5'-CAGAGTAAGAGGC TAAGGTTTACC-3' | ChIP RT-PCR | 25 |
| GAPDH-F | 5'-AAAAGCGGGGAG AAAGTAGG-3' | ChIP RT-PCR | 26 |
| GAPDH-R | 5'-CTAGCCTCCCGGGTTT CTCT-3' | ChIP RT-PCR | 27 |
| HPRT-5 | 5'-TGACACTGGCAAAACA ATGCA-3' | Expression RT-PCR | 28 |
| HPRT-3 | 5'-GGTCCTTTTCACCAG CAAGCT-3' | Expression RT-PCR | 29 |
| GAPDH-5 | 5'-GTCGGAGTCAACGGA TTTGG-3' | Expression RT-PCR | 30 |
| GAPDH-3 | 5'-AAAAGCAGCCCTGG TGACC-3' | Expression RT-PCR | 31 |
| p53-5 | 5'-CCCAAGCAATGGATG ATTTGA-3' | Expression RT-PCR | 32 |
| p53-3 | 5'-GGCATTCTGGGAGCTT CATCT-3' | Expression RT-PCR | 33 |
| p21-5 | 5'-GGCAGACCAGCATGA CAGATT-3' | Expression RT-PCR | 34 |
| p21-3 | 5'-GCGGATTAGGGCTT CCTCTT-3' | Expression RT-PCR | 35 |

3. miRdicator™ Array Platform

Custom microarrays were produced by printing DNA oligonucleotide probes representing 688 miRNAs (Sanger database, version 9 and additional Rosetta validated and predicted miRs). Each probe carries up to 22-nt linker at the 3' end of the miRNA's complement sequence in addition to an amine group used to couple the probes to coated glass slides. 20 μM of each probe were dissolved in 2×SSC+0.0035% SDS and spotted in triplicate on Schott Nexterion® Slide E coated microarray slides using a Genomic Solutions®BioRobotics MicroGrid II according the MicroGrid manufacturer's directions. 64 negative control probes were designed using the sense sequences of different miRNAs. Two groups of positive control probes were designed to hybridize to miRdicator™ array (1) synthetic spikes small RNA were added to the RNA before labeling to verify the labeling efficiency and (2) probes for abundant small RNA (e.g. small nuclear RNAs (U43, U49, U24, Z30, U6, U48, U44), 5.8 s and 5s ribosomal RNA) are spotted on the array to verify RNA quality.

The slides were blocked in a solution containing 50 mM ethanolamine, 1M Tris (pH 9.0) and 0.1% SDS for 20 min at 500 C, then thoroughly rinsed with water and spun dry.

4. Cy-Dye Labeling of miRNA for miRdicator™ Array

15 µg of total RNA was labeled by ligation of a RNA-linker p-rCrU-Cy-dye (Thomson et al., 2004, Nat Methods 1, 47-53) (Dharmacon) to the 3'-end with Cy3 or Cy5. The labeling reaction contained total RNA, spikes (20-0.1 fmoles), 500 ng RNA-linker-dye, 15% DMSO, 1× ligase buffer and 20 units of T4 RNA ligase (NEB) and proceeded at 40 C for 1 hr followed by 1 hr at 37° C. The labeled RNA was mixed with 3× hybridization buffer (Ambion), heated to 95° C. for 3 min and than added on top of the miRdicator™ array. Slides were hybridize 12-16 hr, followed by two washes with 1×SSC and 0.2% SDS and a final wash with 0.1×SSC.

The array was scanned using an Agilent Microarray Scanner Bundle G2565BA (resolution of 10 µm at 100% power). The data was analyzed using SpotReader software.

5. RNA Extraction, Northern Blot Analysis and Real-Time qRT-PCR

Total RNA was extracting with the miRvana miRNA isolation kit (Ambion) according to the manufacturer's instructions. For Northern blot analysis, RNA was resolved on a 15% acrylamide-bisacrylamide (19:1) gel containing 7M urea in Tris-borate-EDTA (TBE) buffer. Decade marker (Ambion), radiolabeled using the manufacturer's protocol, served as a reference. Electrophoresis was at 20 mA. The gel was stained briefly with ethidium bromide, and RNA was transferred by electroblotting onto a GeneScreen Plus membrane (Perkin Elmer Life Sciences) for 1.5 h at 200 mA in 0.5×TBE. The membrane was UV cross-linked (Stratalinker, Stratagene). After 2 h of prehybridization, the membrane was hybridized overnight in ULTRAhyb-Oligo hybridization buffer (Ambion) at 37° C. with a 50 nM $^{32}$P-end-labeled LNA anti-miR-34a oligonucleotide (Exiqon) probe. The membrane was washed in low stringency wash buffer (Ambion) and exposed to film (Kodak BioMax MS) for 6 h at −70° C.

RNA quantification was performed by real-time qRT-PCR in an ABI PRISM 7300 Sequence Detection System (Applied Biosystems) with SYBR Green Master Mix (Applied Biosystems). For mRNA quantification, cDNA produced with random hexamers and MMLV reverse transcriptase (Promega) from 10 ng of total RNA was subjected to RT-PCR using super SYBR-green ready mix (Applied Biosystems) and specific DNA primers (Table 1 for the EST, Table 2 for p21, Hdm2, GAPDH and HPRT). For small RNAs (U6, 5S, microRNAs), 50 ng total RNA was converted to cDNA using specific primers for reverse transcription (Ambion) and MMLV reverse transcriptase. Relative expression levels were determined by real-time qRT-PCR using super SYBR-green ready mix and specific primers (Ambion). Quantification was done using standard curves. All reactions were performed in duplicate.

6. Western Blotting

Total cell extracts (50 µg protein) were resolved on an SDS-10% polyacrylamide gel, electroblotted to a nitrocellulose membrane (Protran, S&S) and reacted with the appropriate antibodies. Bands were visualized with the ECL chemiluminescence kit (Amersham).

7. Chromatin Immunoprecipitation (ChIP)

ChIP analysis was performed as described (Minsky, 2004), employing the CM1 p53-specific polyclonal antibody or anti-HA polyclonal antibody as a control. The PCR primers listed in the Tables 1 and 2 were used to amplify gene-specific sequences from immunoprecipitated chromatin. Quantification of precipitated DNA was preformed by real-time qPCR, using an ABI PRISM 7300 Sequence Detection System. Results were normalized to input DNA.

8. Luciferase Assays 24 h before transfection, cells were plated in 12-well dishes at 5×10$^4$ cell/well. All transfections included also a constant amount of Renilla luciferase plasmid for internal control. 24 h post-transfection the cells were incubated for 30 min with 100 µl/well passive lysis buffer (Amersham), and 35 µl from each well were subjected to a dual luciferase assay (Promega) using a LuminoskanAscent apparatus (ThermoLabsystems). All transfections were done in triplicate. Results are presented after normalization to Renilla luciferase activity in the corresponding samples +/−SEM.

9. FACS Analysis

For DNA content analysis, attached cells were trypsinized, combined with the floating cells, washed, fixed in methanol at −20° C., washed again, rehydrated, and then resuspended in PBS containing 50 µg/mL propidium iodide (PI) and 50 µg/mL RNase A. Samples were analyzed by flow cytometry using a FACS sorter (Becton Dickinson).

10. Colony Formation Assays

Cells were transfected with the indicated plasmid combinations. 24 h post-transfection the cultures were trypsinized, and ⅕ of the cells were re-plated and subjected to selection with 1.5 µpuromycin. After 2 weeks, cultures were washed twice with PBS, incubated with methanol for 20 min, stained with Giemsa dye for 30 min, and washed with tap water. Colonies were counted visually.

11. Statistical Analysis Statistical analysis was performed with the Prism 4 software (GraphPad Software, Inc., San Diego, Calif.).

Example 2 p53-dependent Differential Expression of microRNAs

Figure 7A:
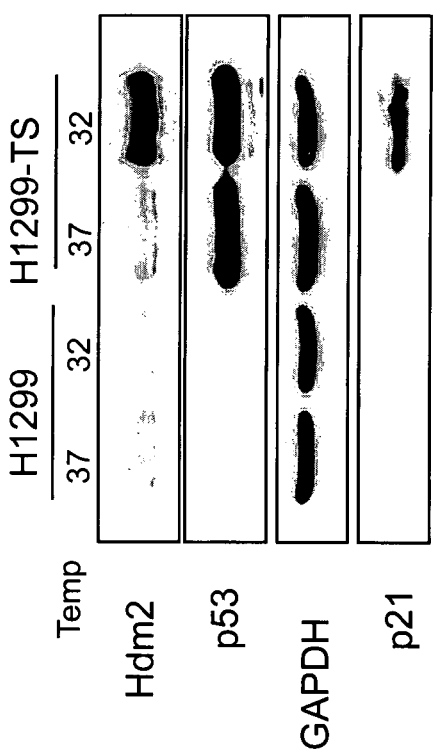

To determine whether p53 can regulate the expression of specific microRNAs, we employed a clone of p53-null H1299 lung cancer cells stably transfected with an expression plasmid for the temperature sensitive p53 mutant p53Val135 (H1299-TS). The p53Val135 protein assumes wild type (wt) p53 conformation when the cells are shifted to the permissive temperature of 32° C. (Michalovitz, 1990), resulting in activation of wt p53 biochemical and biological functions. As seen in FIGS. 7A,C, such shift indeed led to induction of classical transcriptional targets of p53, such as p21 and Mdm2, at both protein and RNA levels. The effect was p53-specific, as it was not observed in parental H1299 cells upon a similar shift. RNA was prepared from both 111299 and H1299-TS cell lines, grown at either 32° C. or 37° C. The four RNA samples were hybridized on two miRdicator™ arrays as described (experimental procedures). Probes were designed for about 700 human miRs including all miRs registered in Sanger database version 9.0. H1299-TS cells expressing active p53 at the permissive temperature of 32° C. exhibited markedly higher expression levels of several miRs, most prominent among them being miR-34a (SEQ ID NO: 1) which was upregulated more than 10-fold following p53 activation (FIG. 1). miRs 638 (SEQ ID NO: 2), 37° C. (SEQ ID NO: 3), 492 (SEQ ID NO: 4), 126 (SEQ ID NO: 5), 140 (SEQ ID NO: 6), 491 (SEQ ID NO: 7) and 296 (SEQ ID NO: 8) were also noticeably up-regulated in the presence of activated p53. Slightly higher expression of background and nonspecific probes compared to the non-permissive temperature was also observed (FIG. 1, squares); this may be due to adverse secondary effects of extended p53 activation. No significant difference in expression of specific miRs was found in the parental H1299 cells when shifted from 37° C. to 32° C. (FIG. 8A). miR-199a (SEQ ID NO: 9) was significantly upregulated in H1299-TS compared to 111299 cultured in 37° C. (FIG. 8B), and was downregulated in H1299-TS in the presence of active p53 compared to the non-permissive temperature (FIG. 1).

Example 3 miR-34a is Activated by p53

Figure 2A:
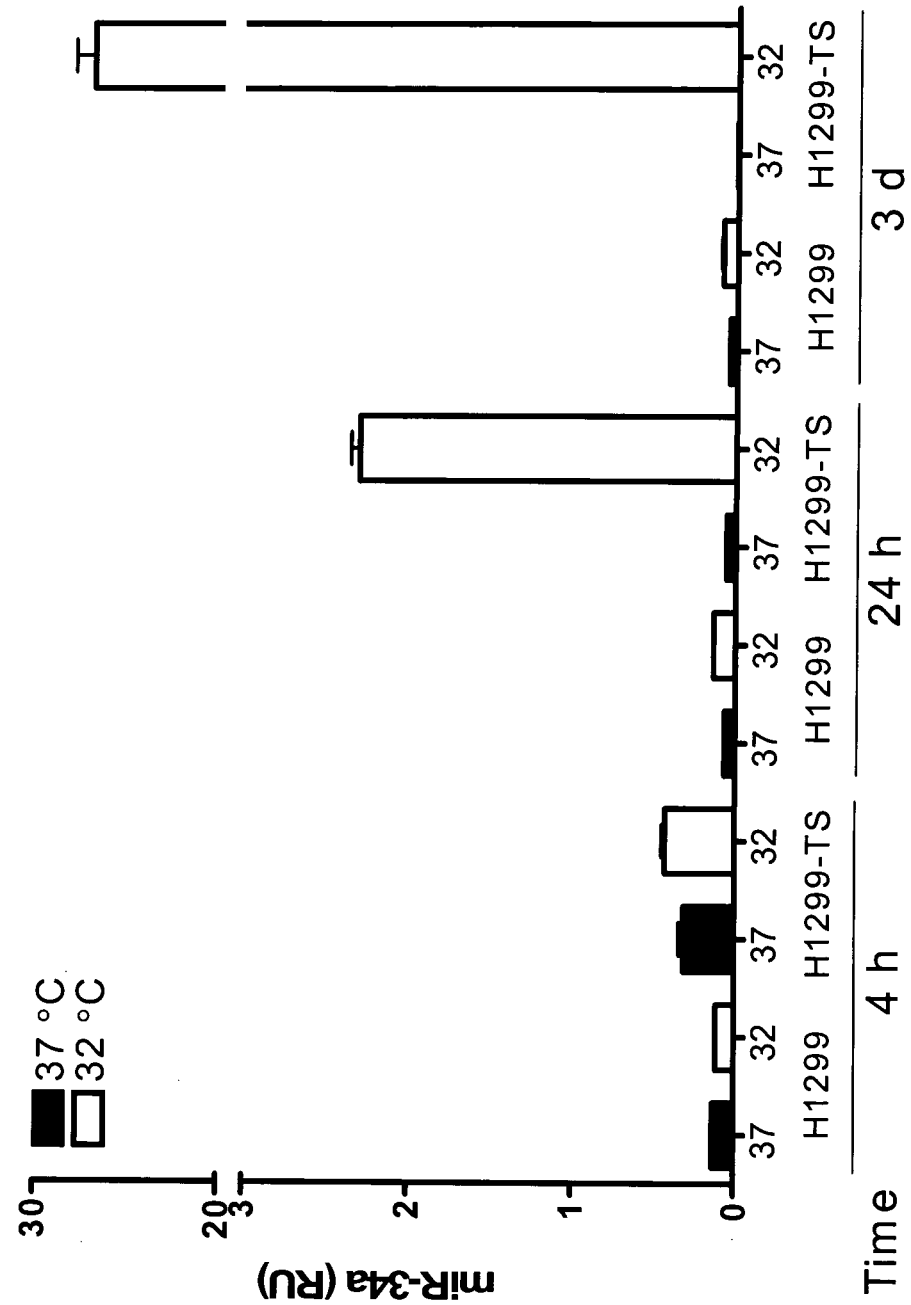
FIG. 2 shows the induction of the expression of miR-34a by wt p53.
Figure 7B:
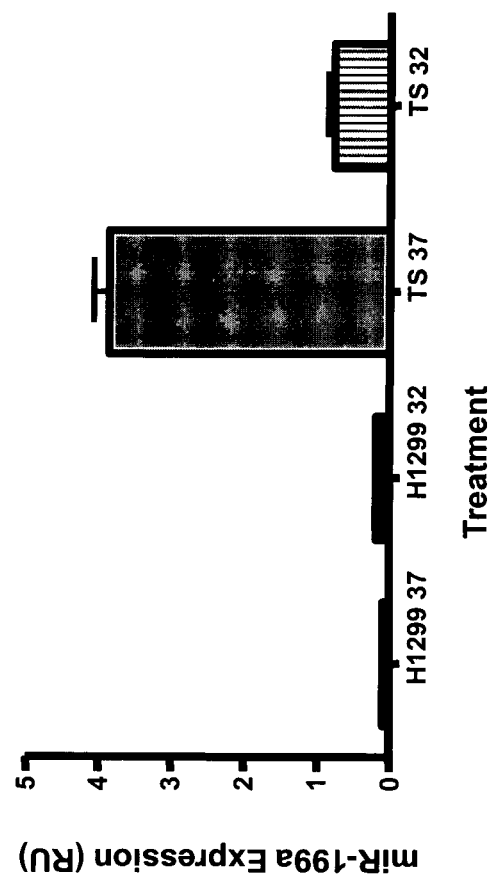
Figure 7C:
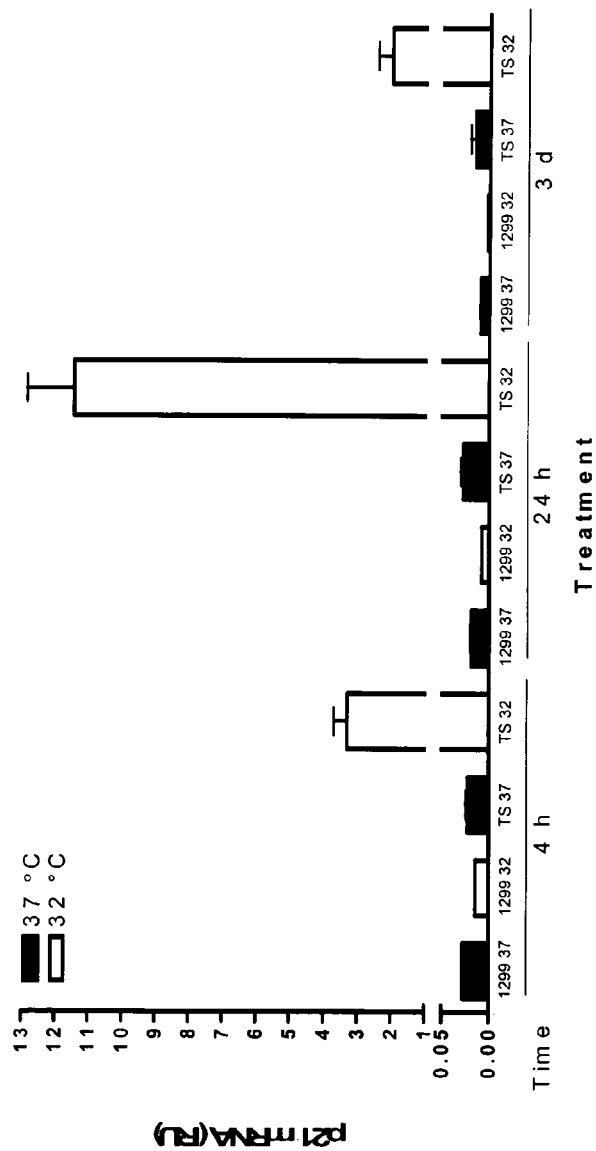
Figure 7D:
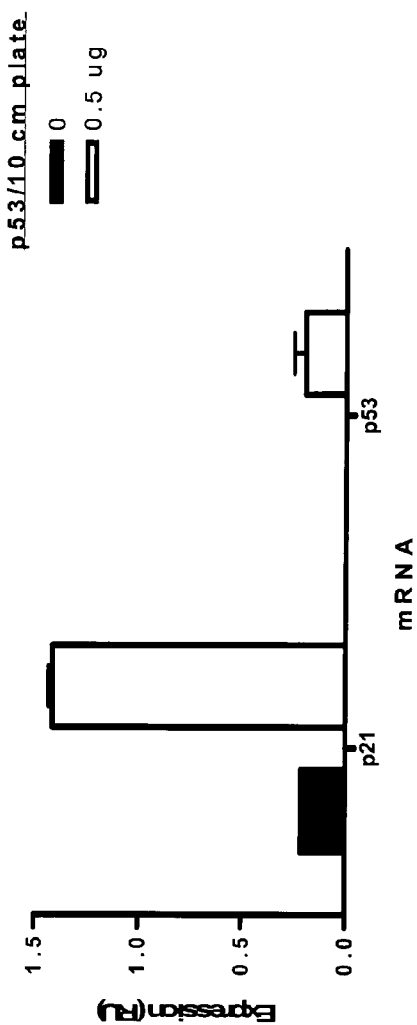

The results of the miRdicator™ array were further validated by quantitative methods. miR-199a (SEQ ID NO: 9) levels were indeed reduced several fold when H1299-TS cells were shifted to 32° C. (FIG. 7B). However, comparison with the p53-null parental H1299 cells suggested that this was due to a strong induction of miR-199a expression by the p53Val135 protein at the non-permissive temperature of 37° C., which was attenuated at 32° C. This is consistent with a possible gain-of-function effect of mutant p53, which deserves further investigation.

miR-34a levels were found to increase dramatically in a p53-dependent manner, as measured by miRdicator™ array (FIG. 1), Real-Time RT-PCR (qRT-PCR; FIG. 2A) and Northern blot analysis (FIG. 2B). The kinetics of miR-34a induction following p53 activation at 32° C. (FIG. 2A) were slower than those of p21 mRNA (FIG. 7C). Similar results were obtained with another independently established H1299-TS cell clone (data not shown). To further rule out clonal variation effects, H1299 cells were transiently transfected with wtp53. While basal miR-34a levels were almost undetectable, exogenous p53 overexpression led to a 20 fold increase in endogenous miR-34a (FIG. 2C, white bar), which was even higher than the induction of p21 mRNA in the same experiment (FIG. 7D).

Figure 2E:
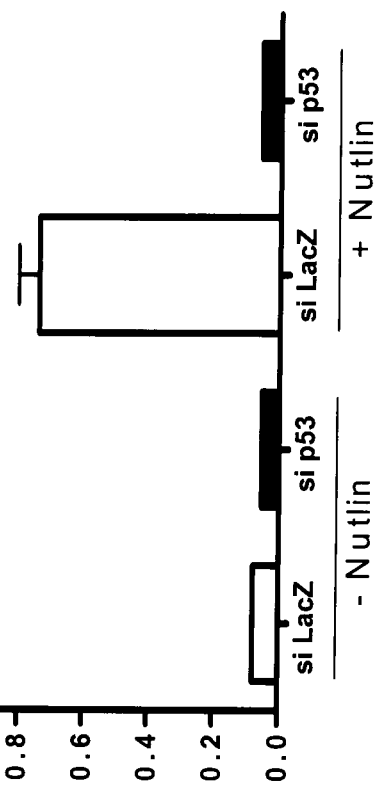
Figure 2D:
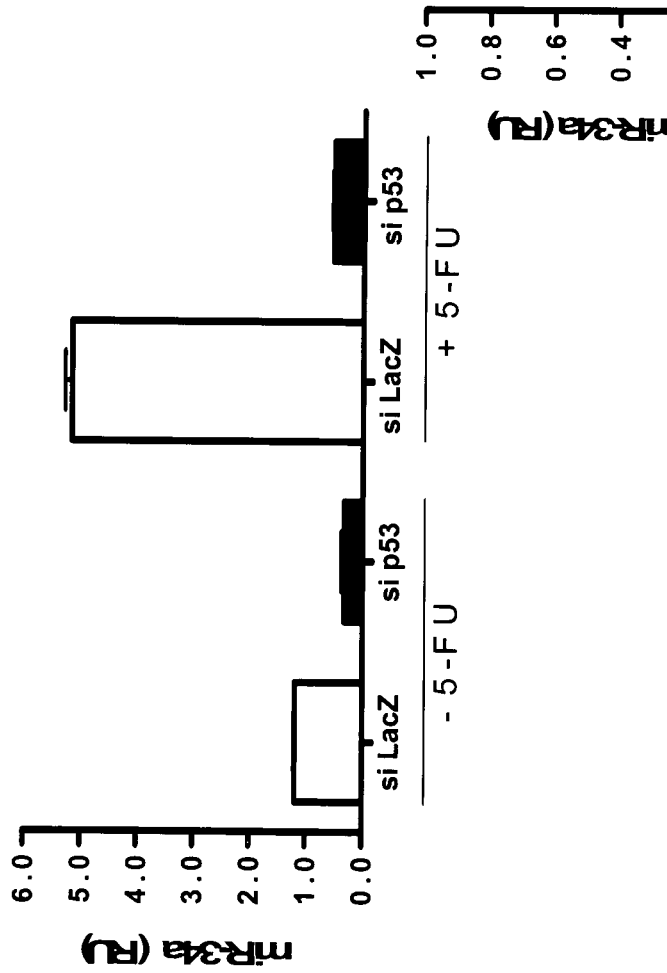
Figure 8A:
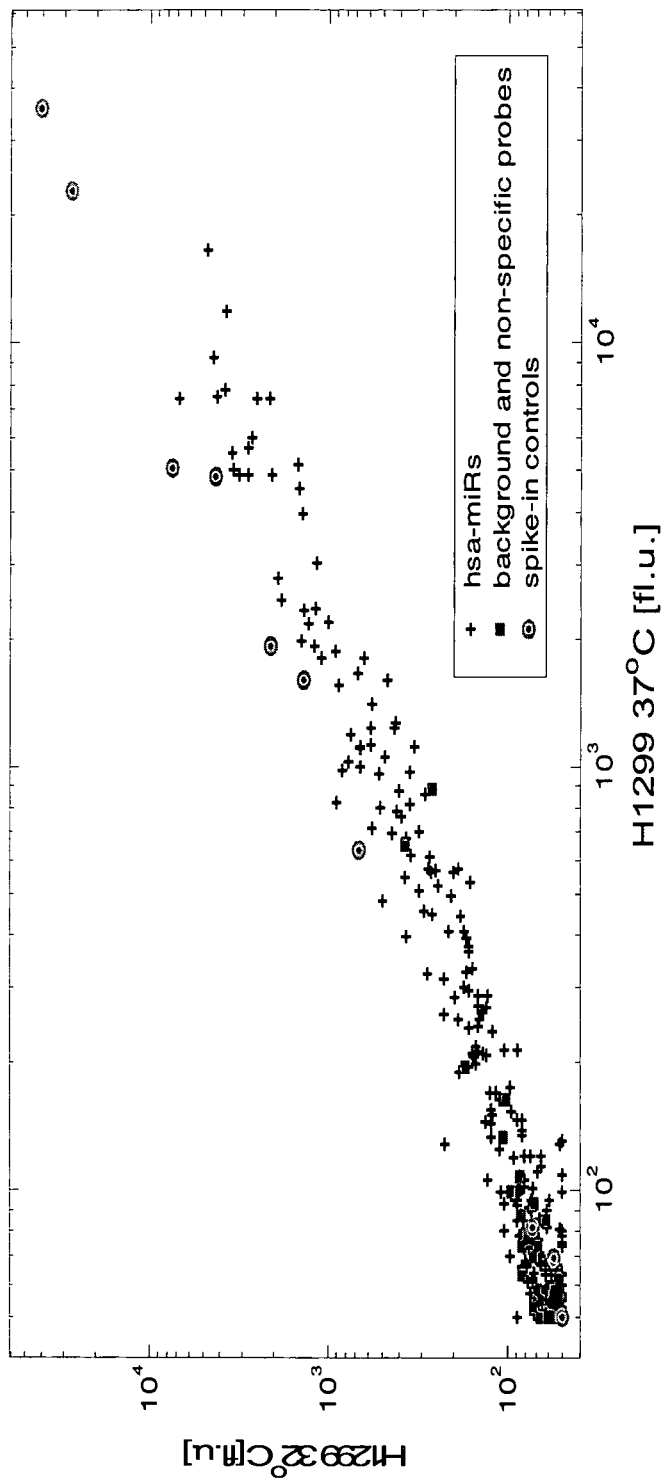

We next asked whether miR-34a can also be induced by physiological levels of p53. As seen in FIG. 2, stable shRNA-mediated knockdown of basal endogenous wtp53 (sip53) resulted in a moderate downregulation of miR-34a in HCT116 (panel D) and U2OS (panel E) cells. The impact of p53 on miR-34a expression became more pronounced when the endogenous wtp53 was further activated by treatment of HCT116 cells with 5 fluorouracil (5-FU; FIG. 2D), or treatment of U2OS cells with Nutlin-3 (Tovar, 2006), which interferes with the binding of p53 to its negative regulator Mdm2 (FIG. 2E); the effects of both drugs on the levels of p53, p21 and Mdm2 proteins are shown in FIGS. 8C,D. The induction of miR-34a by those drugs was comparable to that of p21 mRNA (FIGS. 8A,B). Altogether, these observations strongly argue that p53 is a positive regulator of miR-34a expression.

Example 4 miR-34a is Produced by Splicing of a long p53-Regulated Primary Transcript

The pri-miR-34a (SEQ ID NO: 10) is located on the negative strand of human chromosome 1 (FIG. 3A, upper left end). We performed a search for putative p53 binding sites (p53BS) within the genomic region comprising miR-34a, using the p53 MH algorithm (Hoh, 2002). The only site with a very high score (25.85, 100% of maximal score; indicated in bold letters in FIG. 3B) was found approximately 30 Kb upstream to the mature miR-34a (asterisk in FIG. 3A). This site is located within a CpG island and in very close proximity to the 5' end of a recently reported EST (accession number DB286351; triangle in FIG. 3A). Moreover, this genomic region contains a validated p53 binding site (p53BS), identified by ChIP-PET (Wei, 2006). The reported EST sequence consists of two exons, separated by an intron of about 30 Kb, with the miR-34a precursor located in the second exon (FIGS. 3A,B); hereafter, we will refer to it as pm34a-EST (pri-mIR-34 EST). As this EST was reported only once, we wished to confirm its existence in H1299-TS cells. To that end semiquantitative RT-PCR was performed on cDNA synthesized on RNA extracted from H1299-TS cells maintained at 32° C. The positions of the various PCR primers, relative to the two exons and the mature miR-34a, are indicated in FIG. 3B. As seen in FIG. 3C, products of lengths predicted from the EST sequence were indeed obtained. Notably, a DNA product of the correct length was obtained even with a reverse primer located 30 nucleotides downstream to the 3' end of the published EST (FIG. 3C, lanes 2,4,6), indicating that the RNA extends beyond that point.

Figure 3F:
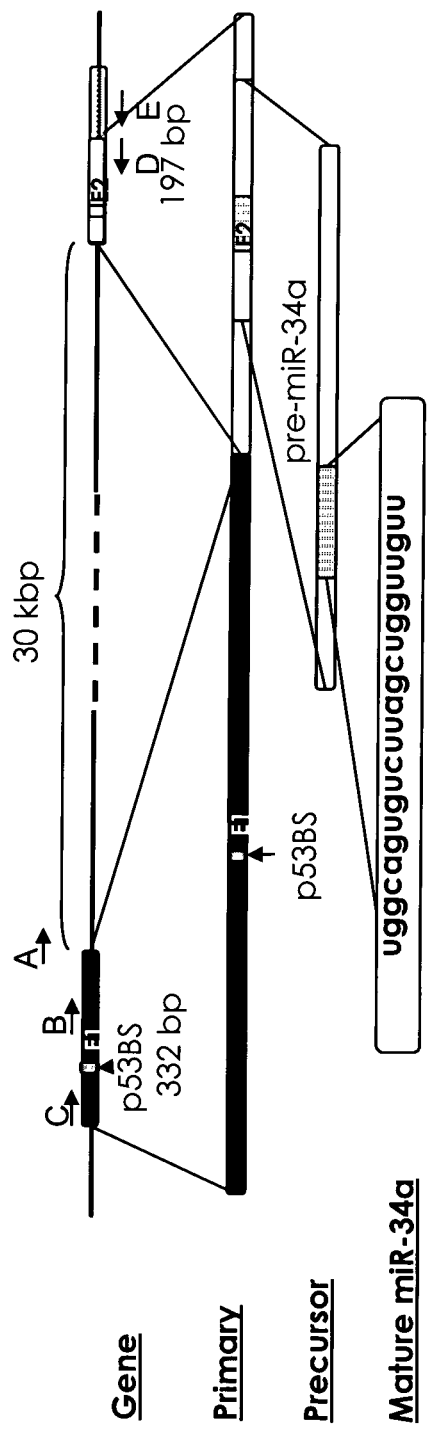
Figure 4A:
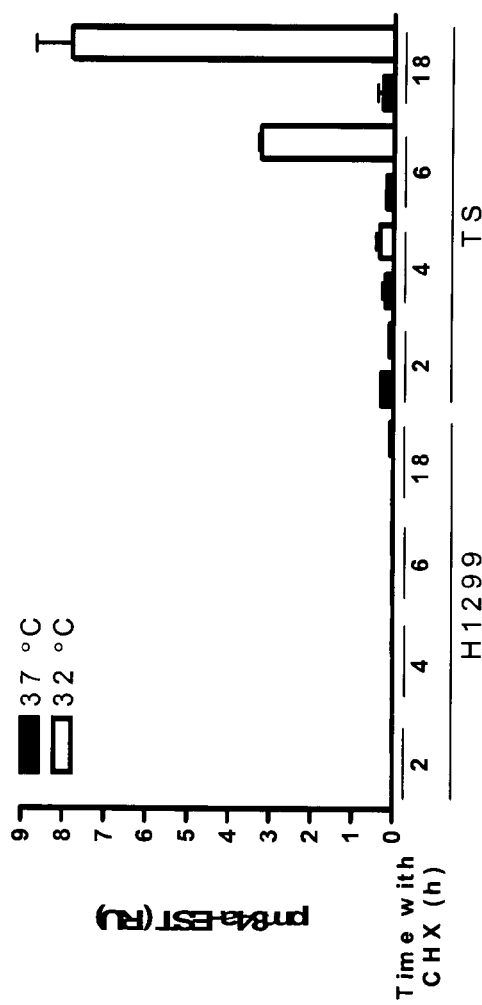
Figure 4B:
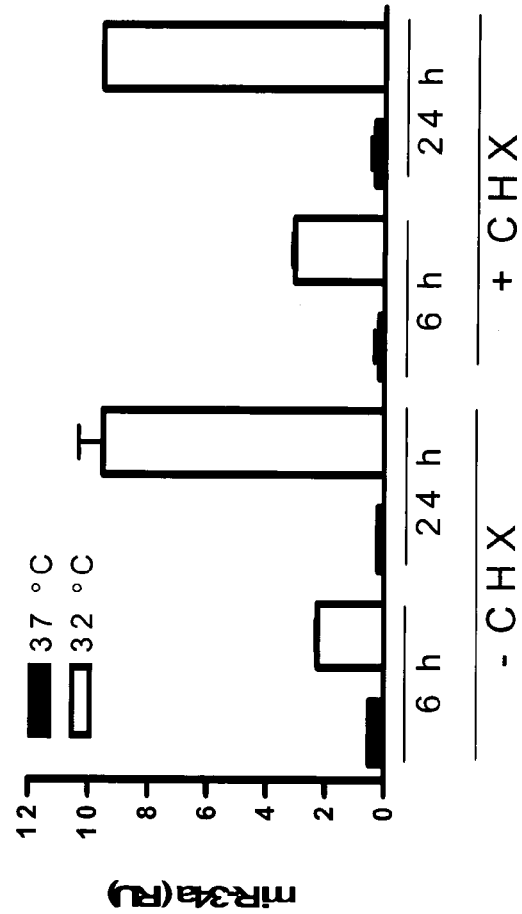
Figure 4C:
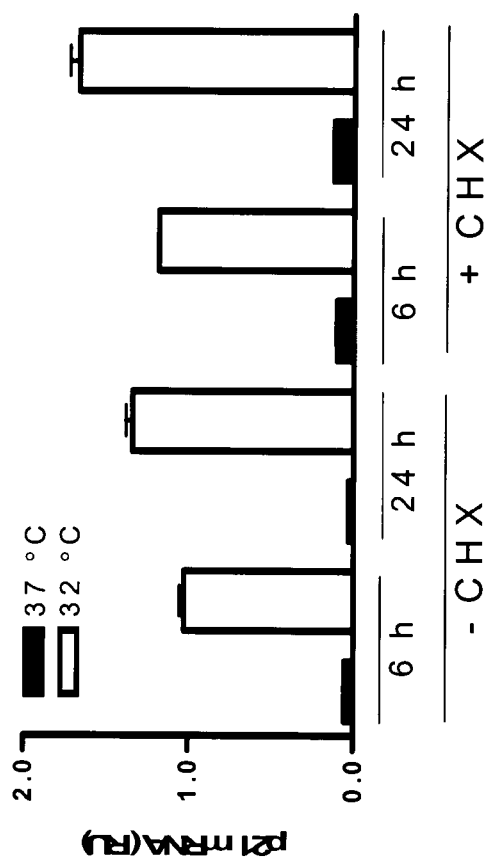
Figure 4D:
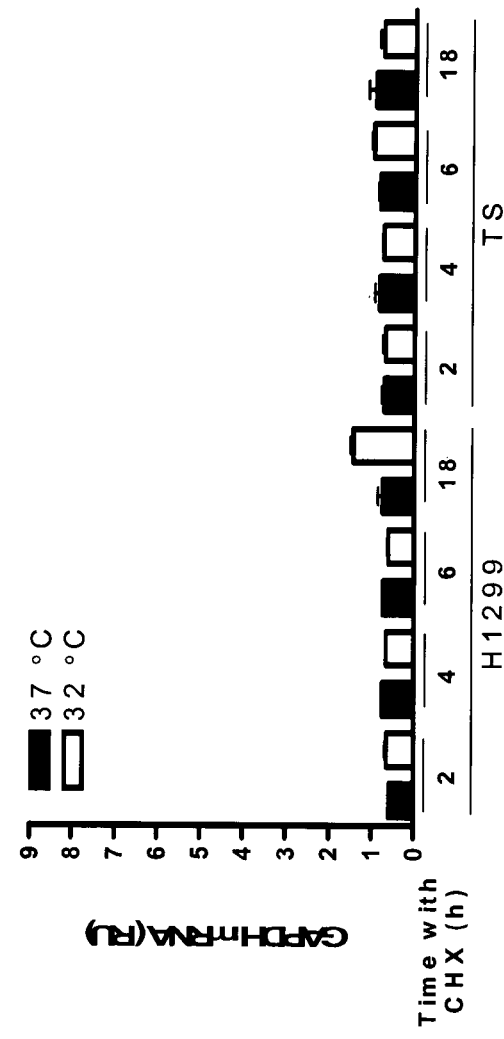

These results demonstrated that the primary transcript of the miR-34a gene undergoes splicing to excise a 30 Kb intron, presumably before being processed into the mature miR. To find out whether transcription of pm34a-EST is also positively regulated by p53, qRT-PCR was performed on RNA of H1299-TS cells, employing primers designed to detect the spliced RNA (see FIGS. 3B,F for primer locations). As seen in FIG. 3D, p53 activation at 32° C. resulted in production of abundant amounts of such RNA. Furthermore, abrogation of endogenous wt p53 downmodulated the amounts of the spliced RNA in several different cell lines (FIG. 3E). These data imply that p53 induces the transcription of a large mRNA, which is subsequently spliced and further processed into mature miR-34a (FIG. 3F). It should be noted that the data does not rule out the possible existence of additional exons in the primary transcript; in fact, several ESTs have been reported that suggest splicing of the present exon 1 to one or two additional upstream exons (data not shown).

Example 5

Expression of pm34a-EST and of miR-34a is Directly Stimulated by p53

The relatively slow accumulation of miR-34a upon p53 induction might suggest that this is a secondary consequence of p53 activation, rather than a direct transcriptional effect. To distinguish between these possibilities, induction of pm34a-EST and miR-34a was assessed in the presence of the protein synthesis inhibitor cycloheximide (CHX). CHX did not prevent the induction of either pm34a-EST (FIG. 4A) or mature miR-34a (FIG. 4B and FIG. 9) in H1299-TS cells shifted to 32° C., nor did it affect p21 mRNA induction (panel C). Neither of the treatments affected control GAPDH mRNA levels (panel D). Hence, upregulation of pm34a-EST and mature miR-34a by p53 does not require de novo protein synthesis, implying that p53 is a direct transcriptional activator of the corresponding gene.

Figure 5A:
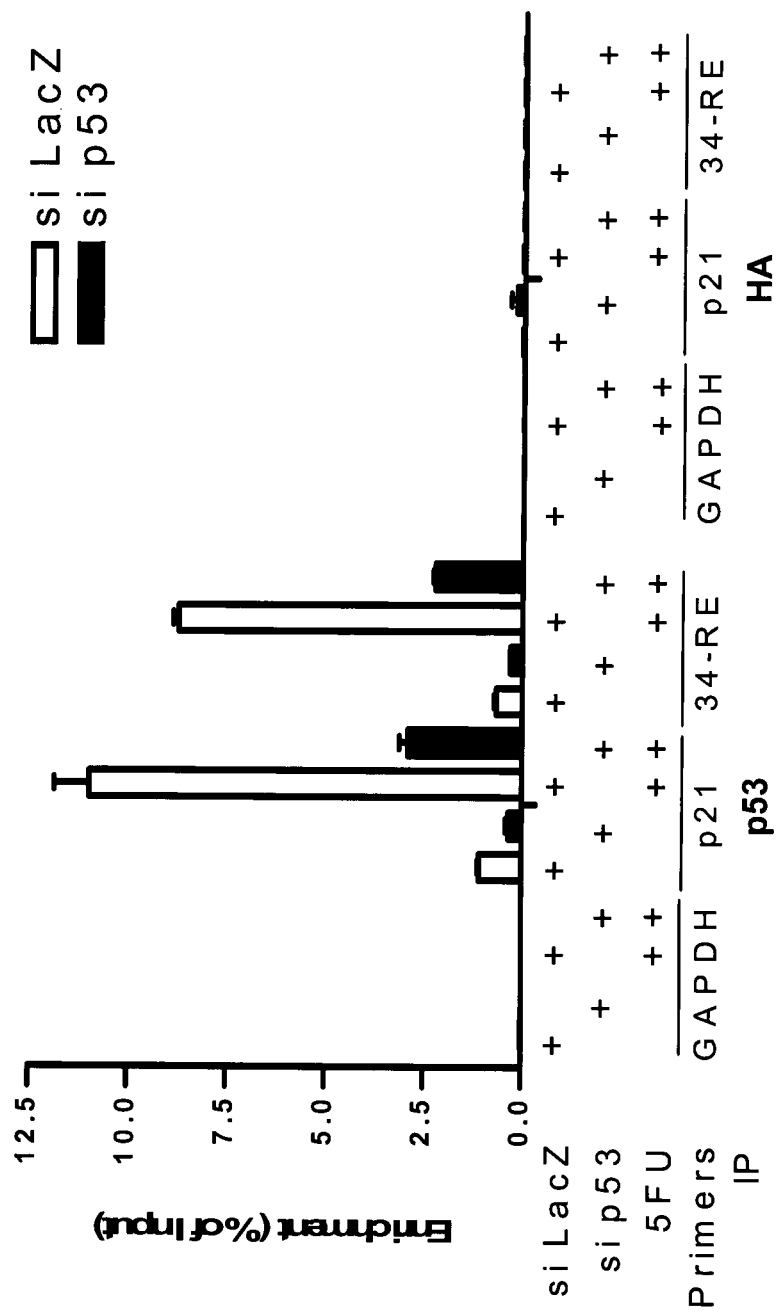
Figure 5B:
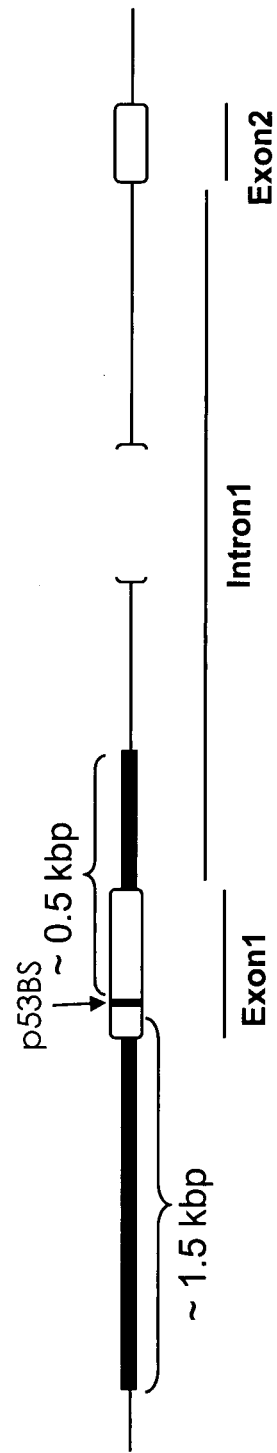
Figure 8B:
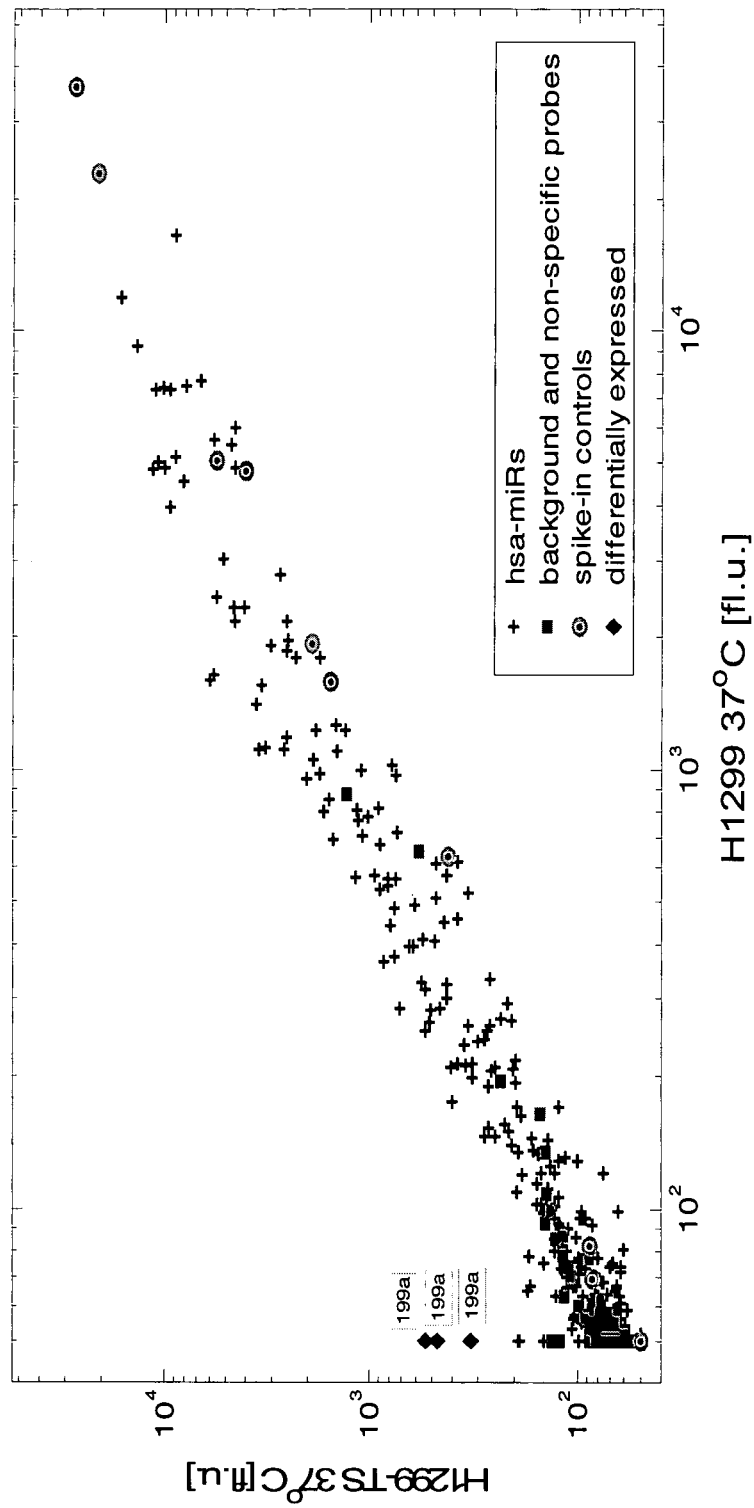

As discussed above, the first exon of pm34a-EST encompasses a perfect p53BS. To determine whether p53 can indeed bind to this site, Chromatin Immunoprecipitation (ChIP)

analysis was performed on HCT116 cells where endogenous p53 had been knocked down by stable expression of p53 shRNA (sip53); cells transfected with LacZ shRNA (siLacZ), harboring unperturbed levels of wtp53, served as a control. Cells were assayed without or with further induction of p53 by 5-FU. The impact of p53 knockdown on the levels of p53, p21 and Mdm2 proteins is shown in FIG. 8B. As expected, immunoprecipitation of chromatin with antibodies against p53, but not control HA antibodies, was strongly enriched for the 5' p53BS of the p21 gene (FIG. 5A). Importantly, a comparable enrichment was found for the predicted p53BS residing within the pm34a-EST, but not for the GAPDH gene serving as a negative control. Hence, p53 binds directly to the pm34a-EST p53BS, and this binding is further augmented upon p53 activation by 5-FU.

Figure 5C:
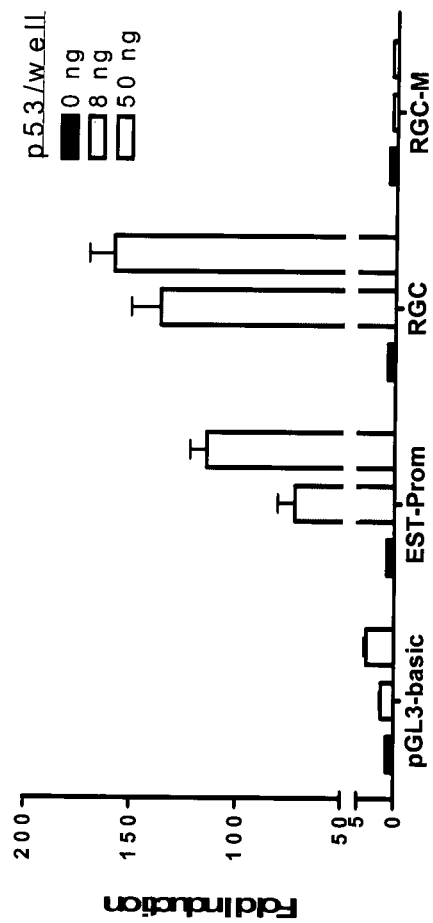
Figure 5D:
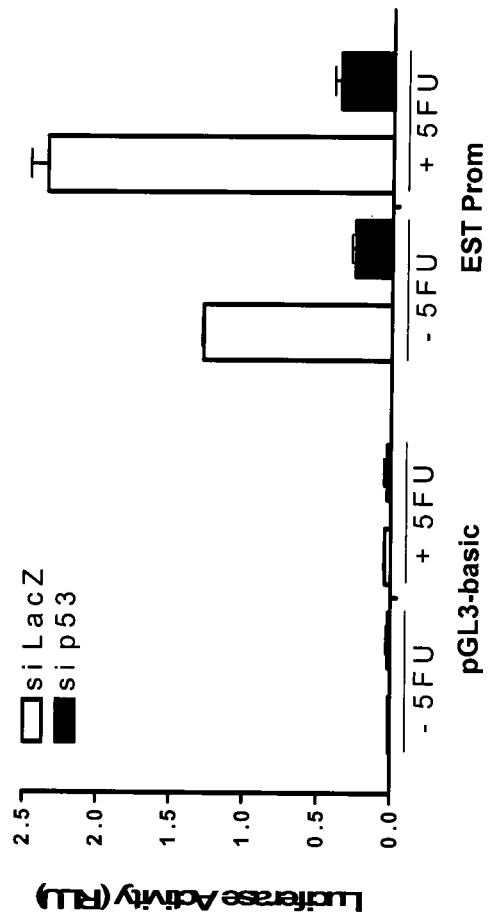

Next, we wished to evaluate the ability of this p53BS to confer p53-dependent transcriptional activation. A region of genomic DNA, comprising the p53BS along with 1.5 Kb of upstream sequences and 0.5 Kb of downstream sequences (FIG. 5B), was cloned in front of the firefly luciferase gene in plasmid pGL3-basic; this is promoterless vector, and promoter activity has to be provided by the cloned DNA fragment. The resultant construct (EST-Prom-luc) was transfected into H1299 cells along with increasing amounts of a wtp53 plasmid. As seen in FIG. 5C, p53 strongly stimulated the activity of EST-Prom-luc (about 20 fold above the control pGL3-basic vector). The extent of stimulation was almost as high as that of a luciferase reporter plasmid carrying 17 tandem repeats of a synthetic p53BS (FIG. 5D, RGC).

To assess the impact of endogenous wtp53 on the transcriptional activity of EST-Prom, this reporter plasmid was transfected into HCT116 cells together with synthetic siRNA oligonucleotides specific for p53 (sip53) or LacZ (siLacZ) as a control. The resultant partial depletion of p53 protein is documented in FIG. 10. Knockdown of p53 caused a better than 3-fold decrease in luciferase expression from EST-Prom-luc (FIG. 5D). 5-FU caused a further mild activation of p53, which led to a nearly twofold increase in luciferase activity in the control (siLacZ) but not the p53-depleted (sip53) cells. Thus, the p53BS located in the first exon of pm34a-EST can bind p53 in vivo and drive p53-dependent transcriptional activation.

Example 6 miR-34a Exerts Antiproliferative and Proapoptotic Effects

Figure 6A:
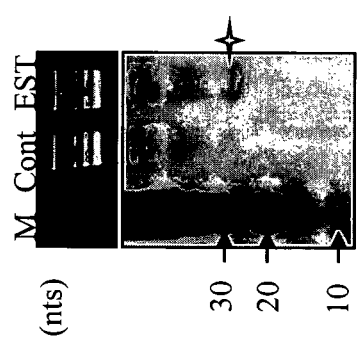
Figure 6B:
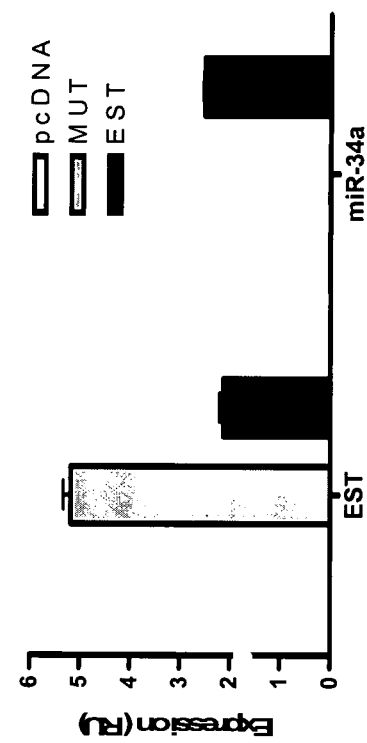
Figure 6C:
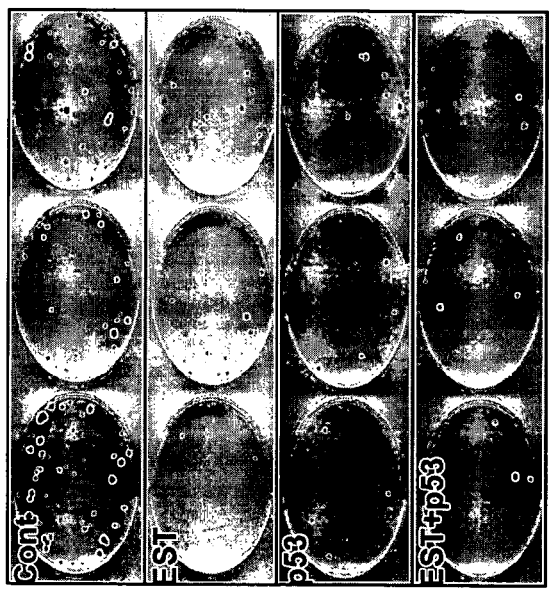
Figure 6D:
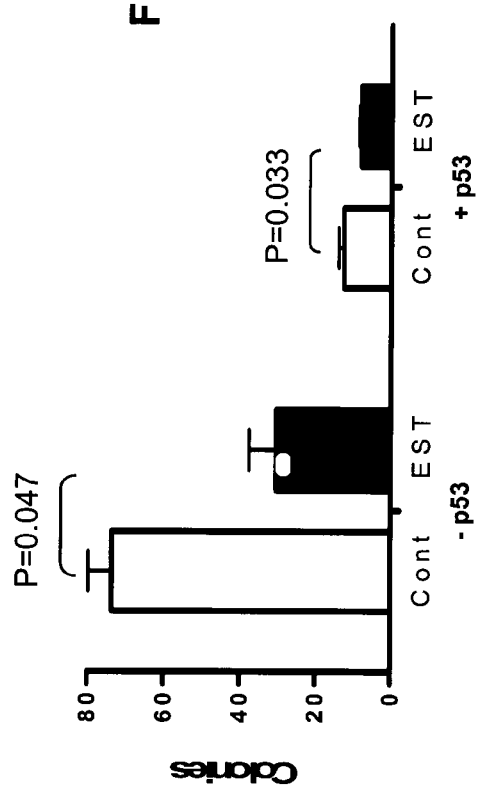
Figure 6G:
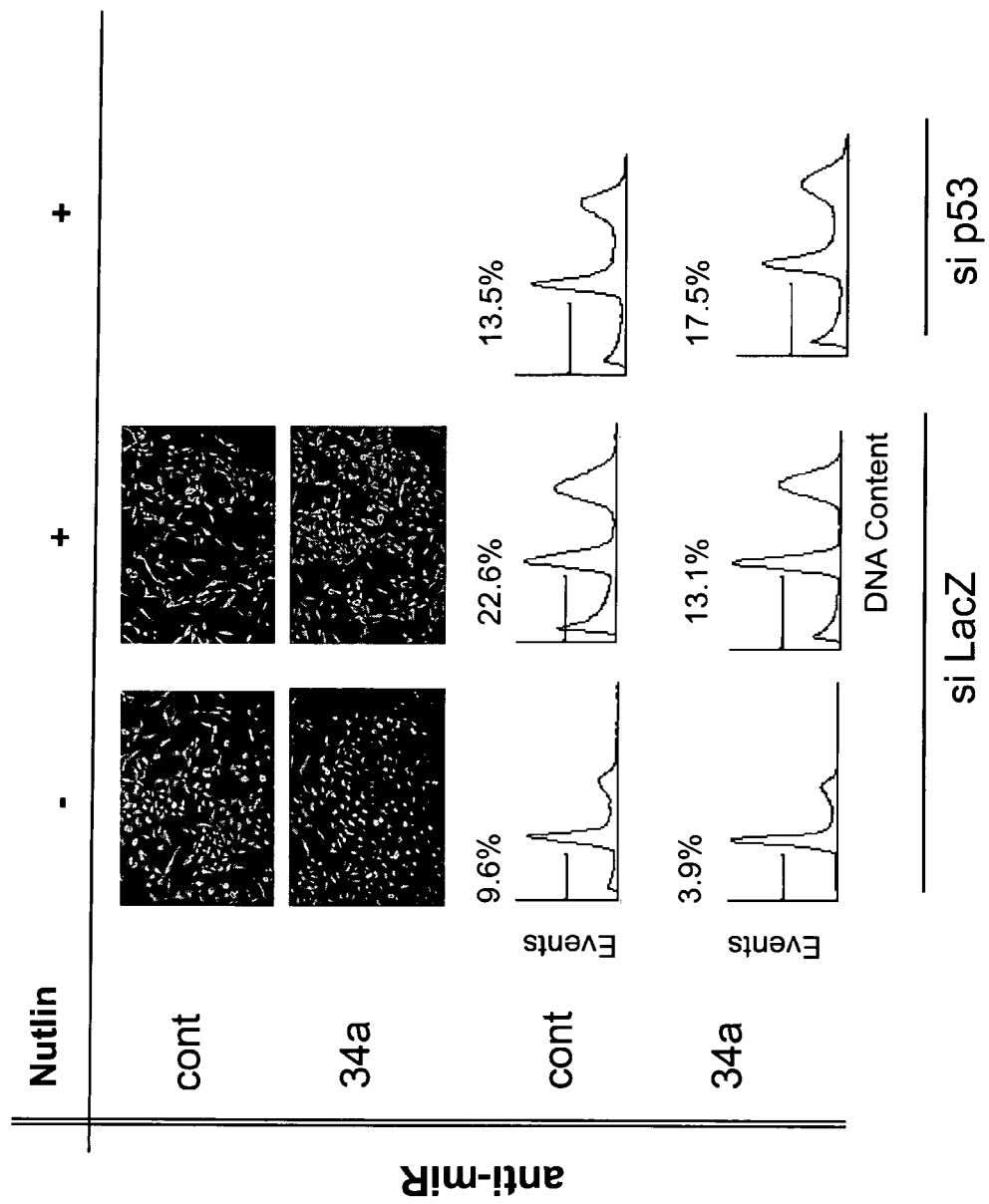

To explore the biological effects of miR-34a, the pm34a-EST sequence was cloned into a mammalian expression vector, giving rise to plasmid pcDNA3-pm34a-EST. Transient transfection of this plasmid into H1299 cells gave rise to substantial production of mature miR-34a, detected by Northern blotting (FIG. 6A) and by qRT-PCR (FIG. 6B, black bar, miR-34a). pcDNA3-pm34a-EST was transfected into H1299 cells together with a plasmid encoding puromycin resistance, and drug resistant colonies were scored 2 weeks later. Overexpression of pcDNA3-pm34a-EST caused a significant reduction in colony number (EST, FIGS. 6C and 6D, representing two independent experiments) relative to the vector control (Cont). Furthermore, although overexpression of wtp53 inhibited colony formation more robustly, addition of pcDNA3-pm34a-EST slightly enhanced this inhibitory effect (EST+p53, FIGS. 6C and 6D).

In addition to the miR-34a precursor, the pm34a-EST sequence also contains an open reading frame (ORF) encoding a hypothetical protein of 133 amino acid residues (FIG. 11). It could thus be argued that this putative protein, rather than miR-34a, was responsible for the observed suppression of colony formation. To address this possibility, mutations were introduced into pcDNA3-pm34a-EST such that the predicted ORF would be preserved, but the secondary structure of the miR-34a precursor would be disturbed in a manner that should prevent its processing into mature miR-34a and change the seed sequence of the miR (mutation positions are underlined in FIG. 11). The resultant plasmid, designated pcDNA3-pm34a-EST-MUT, was indeed incapable of giving rise to mature miR-34a (FIG. 6B, MUT), despite being transcribed at least as efficiently as its non-mutant counterpart (FIG. 6B, EST RNA, compare MUT to EST). Importantly, when transfected either alone or together with wtp53, the wt EST suppressed colony formation more efficiently than its mutant counterpart (FIG. 6E), supporting the conclusion that the mature miR-34a was responsible for at least part of the observed inhibitory effect. Together, these results imply that overexpression of miR-34a can exert antiproliferative effects, as measured by long term clonogenic assays. p53 has well-documented proapoptotic activities. To investigate whether induction of miR-34a might contribute to such activities, we employed a locked nucleic acids (LNA) oligonucleotide complementary to the miR-34a sequence in order to block endogenous miR-34a function in U2OS cells; a corresponding scrambled oligonucleotides (Cont) was used as a control. As seen in FIG. 6F, inhibition of miR-34a (anti-miR34a) led to a decrease in spontaneous apoptosis, presumably due to transfection-induced stress; this was evident microscopically (left panels), as well as by FACS-based detection of cells with sub-G1 DNA content, indicative of apoptosis (right panels). Furthermore, inhibition of miR-34a provided partial protection from the enhanced apoptosis due to treatment with the p53-activating drug Nutlin-3. This effect was p53-dependent, as it was not observed in U2OS cells in which the endogenous wtp53 had been knocked down by stable expression of p53 shRNA (sip53). Together, these data indicate that miR-34a can exert an antiproliferative effect and that at least part of that effect may rely on a proapoptotic activity of this miR.

Example 7 miR-34a Regulates Notch Pathway Activity

In an earlier publication, two putative targets for miR-34a—Notch1 and Delta 1, also called Delta-like 1 (DLL1)—were identified and validated indirectly, using a luciferase reporter assay (Lewis et al., 2003).

Notch is a transmembrane protein receptor that mediates interactions between adjacent cells and regulates cell fate decisions during development. In mammals four Notch genes (Notch1-4) have been cloned. Thus far, six Notch receptor-specific ligands (Delta1, 2, 3 and 4 as well as Jagged1 and 2) have also been identified in mammals (Radtke and Raj, 2003). Notch activation is initiated by interactions with ligands of the Delta and Jagged families and results in cleavage and release of the intracellular region of the Notch receptor followed by its nuclear translocation. In the nucleus it interacts with the transcription factor CBF1 (RBPjk) to transactivate target genes, including Hey1 (Iso et al., 2001). Constitutively active intracellular forms of Notch have been shown to have oncogenic activity and to inhibit p53-mediated cell death (Kim et al., 2006; Mungamuri et al., 2006) by inhibiting p53 phosphorylation and transactivation. On the other hand, there is evidence that p53 indirectly inhibits Notch signaling either by sequestering p300/CBP (Pastorcic and Das, 2000), which is required for Notch activation or by p21-dependent downregulation of presenilin 1 transcription (Roperch et al., 1998), which is necessary for Notch cleavage upon ligand binding. Our findings raise the interesting possibility that p53 may negatively regulate Notch signaling, at least partly, also via enhanced expression of microRNAs that bind and inactivate Notch pathway-related mRNAs.

In addition to the indirectly validated targets for miR-34a, Notch1 and DLL1, Jag1 mRNA is also predicted to have putative target sites for this miR (SEQ ID NOS: 38-41) (FIG. 13A). Because all three mRNAs are predicted to be regulated by miR-34a, we checked the influence of manipulating this miR on the functionality of the Notch pathway.

Figures 13D, 13E:
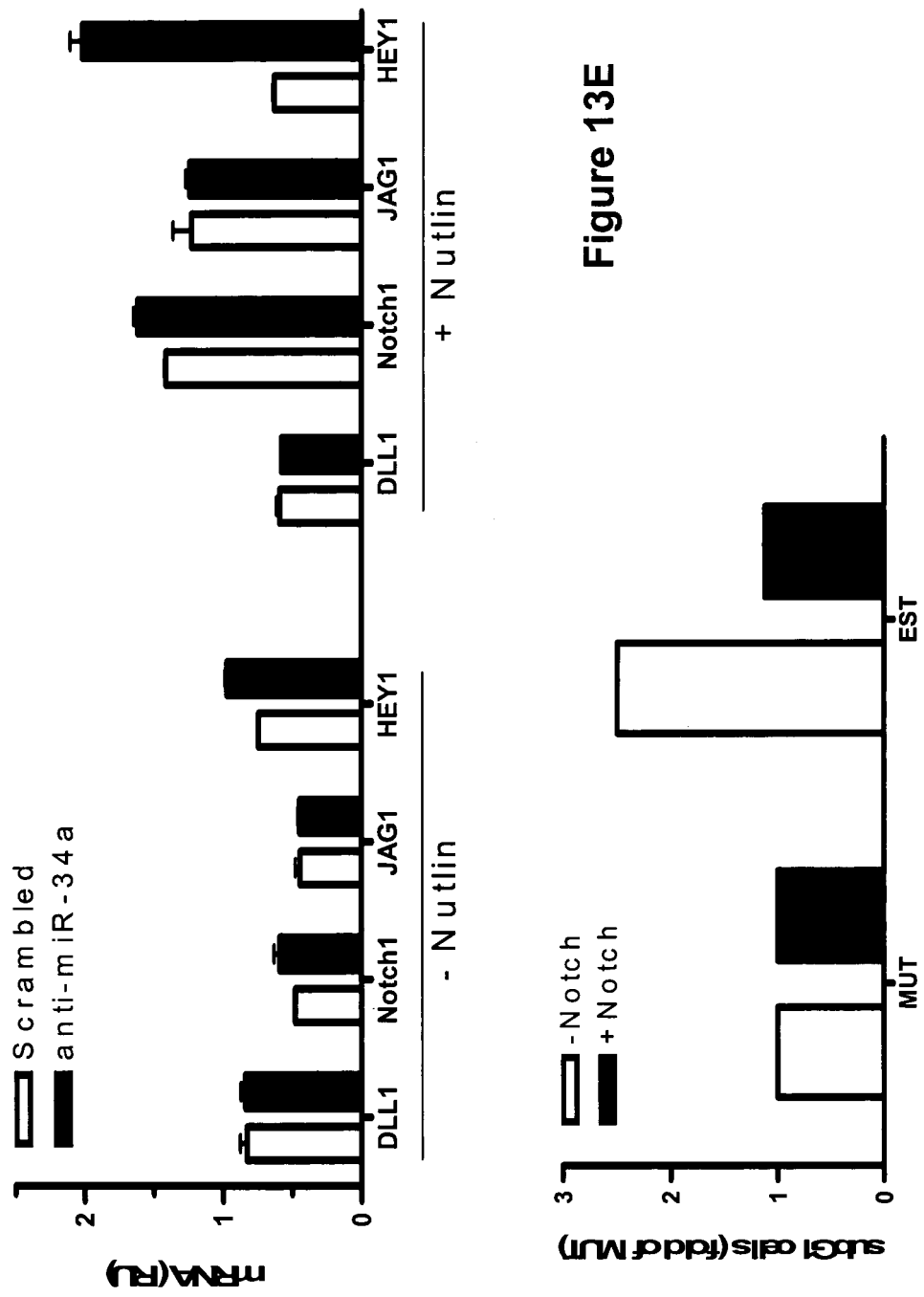

As shown in FIGS. 13B,D, down-regulation of miR-34a by LNA anti-miR-34a: 5'-aacaaccagctaagacactgcca-3' (SEQ ID NO: 36) in either A172 or MCF7 cells had no effect on the mRNA levels of DLL1, Jag1 or Notch1, but resulted in up-regulation of the expression of Hey1, a downstream transcriptional target of Notch pathway activation, as compared to the control scrambled LNA RNA: 5'-gtgtaacacgtctatacgccca-3' (SEQ ID NO: 37). A stronger effect was observed following p53 activation with Nutlin-3 (FIG. 13D), probably because of Nutlin-dependent induction of Jag1 and Notch1 mRNA levels. In both cases, the mRNA expression levels of the three genes were similar when either scrambled or anti-miR-34a LNA oligos were added, suggesting that the differential effect on Hey1 mRNA was achieved due to specific miR-34a down-regulation.

A complementary, opposite effect on Hey1 expression was seen when miR-34a was over-expressed in A172 cells. Despite the absence of any change in the mRNA levels of DLL1, Jag1 and Notch1, miR-34a overexpression led to a reduction in Hey1 mRNA (FIG. 13C).

To find out whether the inhibition of Notch signaling might contribute to the pro-apoptotic effect of miR-34a overexpression, we asked whether this effect can be rescued by experimental upregulation of Notch activity. To that end, MCF7 cells were transfected with either pcDNA3-pm34a-EST (EST) or a mutant, inactive derivative thereof (MUT), with or without addition of a constitutively active Notch expression plasmid, which does not contain the target sequence for miR-34a within its encoded mRNA. The viability of the cells was tested by FACS analysis. As shown in FIG. 13E, the increase in the subG1 population of cells transfected with pcDNA3-pm34a-EST, indicative of apoptosis, was decreased almost to the basal levels when Notch activity was reconstituted exogenously.

Collectively, the data indicate that p53 can regulate the Notch pathway by inducing miR-34a production, which in turn down-regulates the output of this pathway. This effect may be achieved through the combinatorial effect of down-regulating modestly the expression of different components of the pathway. miR-34a may thus be a p53-induced anti-oncogenic guardian of the Notch pathway.

Example 8 miR-34a Regulates Bcl-2 Expression

Figure 14A:
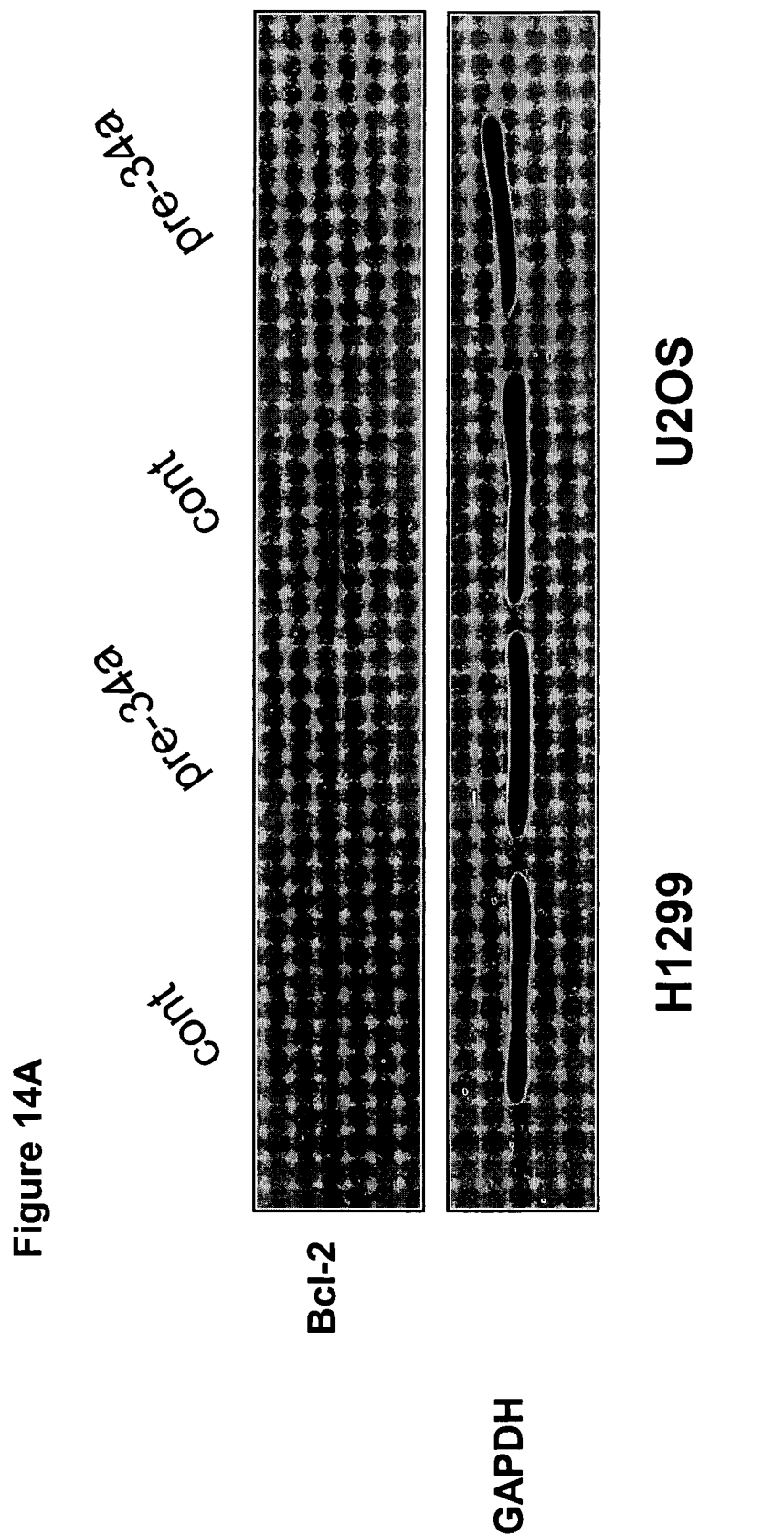

One of the predicted targets of miR-34a is Bcl-2. Proteins in the Bcl-2 family are central regulators of programmed cell death (Danial and Korsmeyer, 2004), and members that inhibit apoptosis, such as Bcl-XL and Bcl-2, are overexpressed in many cancers and contribute to tumor initiation, progression and resistance to therapy (Kirkin et al., 2004). Consistent with Bcl-2 mRNA being a target of miR-34a, we observed that Bcl-2 protein is decreased in miR-34a overexpressing cells (FIG. 14A). However, under those conditions, the decrease in Bcl-2 protein occurred without a measurable decrease in Bcl-2 mRNA (FIG. 14B). Hence, our study confirm that Bcl-2 is an authentic miR-34a target, the different effects on Bcl-2 mRNA imply that in some contexts miR-34a may act exclusively through translational inhibition of Bcl-2 synthesis, as demonstrated by us, whereas in other cases it may also promote the degradation of the corresponding mRNA. The factors that underlie the choice between these different options remain to be elucidated. It is noteworthy that Bcl-2 mRNA is also targeted very efficiently by miR-15a and miR-16-1 (Cimmino et al., 2005). It therefore appears very likely that miR-34a may act in cooperation with these other two candidate tumor-suppressor miRNAs to suppress Bcl-2 expression. This fact, together with the findings that reduced Bcl-2 activity increases sensitivity to anticancer drugs, induces regression of solid tumors (Bruncko et al., 2007; Oltersdorf et al., 2005) and extends animal survival in an experimental cancer model (Letai et al., 2004), raises an option for these microRNAs or derivatives thereof to be considered as a basis for innovative cancer therapies.

Example 9 miR-34a Effects on Tumor Growth In Vivo

H1299 cells stably transfected with empty pcDNA3 vector or with a pcDNA3-based miR-34a expression plasmid are inoculated subcutaneously into CD1 nu/nu mice (male, 4-6-week-old, 10 mice/group) at $5 \times 10^6$ cells per mouse. Tumor growth is assessed by palpation once a week for up to seven weeks or till tumor size reaches a size that calls for termination of the experiment. Tumor size is monitored by caliper measurement, and statistical analysis is performed to determine whether expression of miR-34a has an anti-tumor effect in this setting. At the end of the experiment, tumor specimens are collected for histological analysis as well as for extraction of RNA and analysis of gene expression patterns by Affymetrix microarrays, as well as of miR-34a expression levels (measured by qRT-PCR).

REFERENCES

Barad, O., E. Meiri, A. Avniel, R. Aharonov, A. Barzilai, I. Bentwich, U. Einav, S. Gilad, P. Hurban, Y. Karov, E. K. Lobenhofer, E. Sharon, Y. M. Shiboleth, M. Shtutman, Z. Bentwich, and P. Einat. 2004. MicroRNA expression detected by oligonucleotide microarrays: system establishment and expression profiling in human tissues. Genome Res 14:2486-94.

Bruncko, M., Oost, T. K., Belli, B. A., Ding, H., Joseph, M. K., Kunzer, A., Martineau, D., McClellan, W. J., Mitten, M., Ng, S. C., Nimmer, P. M., Oltersdorf, T., Park, C. M., Petros, A. M., Shoemaker, A. R., Song, X., Wang, X., Wendt, M. D., Zhang, H., Fesik, S. W., Rosenberg, S. H. and Elmore, S. W. 2007. Studies leading to potent, dual inhibitors of Bcl-2 and Bcl-xL. *J Med Chem,* 50, 641-662.

Cimmino, A., Calin, G. A., Fabbri, M., Iorio, M. V., Ferracin, M., Shimizu, M., Wojcik, S. E., Aqeilan, R. I., Zupo, S., Dono, M., Rassenti, L., Alder, H., Volinia, S., Liu, C. G., Kipps, T. J., Negrini, M. and Croce, C. M. 2005. miR-15 and miR-16 induce apoptosis by targeting BCL2. *Proc Natl Acad Sci USA,* 102, 13944-13949.

Danial, N. N. and Korsmeyer, S. J. 2004. Cell death: critical control points. *Cell,* 116, 205-219.

Hoh, J., Jin, S., Parrado, T., Edington, J., Levine, A. J., and Ott, J. (2002). The p53 MH algorithm and its application in detecting p53-responsive genes. Proc Natl Acad Sci USA 99, 8467-8472.

Iso, T., Sartorelli, V., Chung, G., Shichinohe, T., Kedes, L., and Hamamori, Y. (2001). HERP, a new primary target of Notch regulated by ligand binding. Mol Cell Biol 21, 6071-6079.

Kern, S. E., Kinzler, K. W., Bruskin, A., Jarosz, D., Friedman, P., Prives, C., and Vogelstein, B. (1991). Identification of p53 as a sequence-specific DNA-binding protein. Science 252, 1708-1711.

Kim, S. B., Chae, G. W., Lee, J., Park, J., Tak, H., Chung, J. H., Park, T. G., Ahn, J. K., and Joe, C. O. (2006). Activated Notch1 interacts with p53 to inhibit its phosphorylation and transactivation. Cell Death Differ. Advance online publication.

Kirkin, V., Joos, S, and Zornig, M. (2004) The role of Bcl-2 family members in tumorigenesis. *Biochim Biophys Acta*, 1644, 229-249.

Letai, A., Sorcinelli, M. D., Beard, C. and Korsmeyer, S. J. (2004) Antiapoptotic BCL-2 is required for maintenance of model leukemia. *Cancer Cell*, 6, 241-249.

Lewis, B. P., Shih, I. H., Jones-Rhoades, M. W., Bartel, D. P., and Burge, C. B. (2003). Prediction of mammalian microRNA targets. Cell 115, 787-798.

Michalovitz, D., Halevi; O., and Oren, M. (1990). Conditional inhibition of transformationand of cell proliferation by temperature-sensitive mutant of p53. Cell 62, 671-680.

Minsky, N., and Oren, M. (2004). The RING domain of Mdm2 mediates histone ubiquitylation and transcriptional repression. Mol Cell 16, 631-639.

Mungamuri, S. K., Yang, X., Thor, A. D., and Somasundaram, K. (2006). Survival signaling by Notch1: mammalian target of rapamycin (mTOR)-dependent inhibition of p53. Cancer Res 66, 4715-4724.

Oltersdorf, T., Elmore, S. W., Shoemaker, A. R., Armstrong, R. C., Augeri, D. J., Belli, B. A., Bruncko, M., Deckwerth, T. L., Dinges, J., Hajduk, P. J., Joseph, M. K., Kitada, S., Korsmeyer, S. J., Kunzer, A. R., Letai, A., Li, C., Mitten, M. J., Nettesheim, D. G., Ng, S., Nimmer, P. M., O'Connor, J. M., Oleksijew, A., Petros, A. M., Reed, J. C., Shen, W., Tahir, S. K., Thompson, C. B., Tomaselli, K. J., Wang, B., Wendt, M. D., Zhang, H., Fesik, S. W. and Rosenberg, S. H. (2005) An inhibitor of Bcl-2 family proteins induces regression of solid tumours. *Nature*, 435, 677-681.

Pastorcic, M., and Das, H. K. (2000). Regulation of transcription of the human presenilin-1 gene by ets transcription factors and the p53 protooncogene. J Biol Chem 275, 34938-34945.

Radtke, F., and Raj, K. (2003). The role of Notch in tumorigenesis: oncogene or tumour suppressor? Nature Rev Cancer 3, 756-767.

Raver-Shapira, N., Marciano, E., Meiri, E., Spector, Y., Rosenfeld, N., Moskovits, N., Bentwich, Z. and Oren, M. (2007) Transcriptional Activation of miR-34a Contributes to p53-Mediated Apoptosis. *Mol Cell*, 26, 731-743.

Roperch, J. P., Alvaro, V., Prieur, S., Tuynder, M., Nemani, M., Lethrosne, F., Piouffre, L., Gendron, M. C., Israeli, D., Dausset, J., et al. (1998). Inhibition of presenilin 1 expression is promoted by p53 and p21WAF-1 and results in apoptosis and tumor suppression. Nature Med 4, 835-838.

Tovar, C., Rosinski, J., Filipovic, Z., Higgins, B., Kolinsky, K., Hilton, H., Zhao, X., Vu, B. T., Qing, W., Packman, K., et al. (2006). Small-molecule MDM2 antagonists reveal aberrant p53 signaling in cancer: Implications for therapy. Proc Natl Acad Sci USA 103, 1888-1893.

Wei, C. L., Wu, Q., Vega, V. B., Chiu, K. P., Ng, P., Zhang, T., Shahab, A., Yong, H. C., Fu, Y., Weng, Z., et al. (2006). A global map of p53 transcription-factor binding sites in the human genome. Cell 124, 207-219.

Xi, Y., Shalgi, R., Fodstad, O., Pilpel, Y., and Ju, J. (2006). Differentially regulated micro-RNAs and actively translated messenger RNA transcripts by tumor suppressor p53 in colon cancer. Clin Cancer Res 12, 2014-2024.

C Welch, Y Chen and R L Stallings (2007). MicroRNA-34a functions as a potential tumor suppressor by inducing apoptosis in neuroblastoma cells. Oncogene, 1-6.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

---

The invention claimed is:

1. A method of inducing tumor cell apoptosis, wherein the tumor is a non-small cell lung carcinoma (NSCLC), comprising administering to a subject in need thereof a therapeutically effective amount of a composition comprising a nucleic acid, wherein the nucleic acid comprises SEQ ID NO: 1, wherein the NSCLC is p53 negative, and wherein the nucleic acid is encapsulated in a liposome.

2. The method of claim 1 wherein the composition is administered in combination with a first anticancer agent, radiotherapy, or combinations thereof.

3. The method of claim 2 wherein the composition is administered in combination with a second anticancer agent.

* * * * *

SEQUENCE LISTING

```
<160> NUMBER OF SEQ ID NOS: 54

<210> SEQ ID NO 1
<211> LENGTH: 23
<212> TYPE: RNA
<213> ORGANISM: Homo sapiens

<400> SEQUENCE: 1
uggcaguguc uuagcugguu guu                                            23

<210> SEQ ID NO 2
<211> LENGTH: 25
<212> TYPE: RNA
<213> ORGANISM: Homo sapiens

<400> SEQUENCE: 2
agggaucgcg ggcggguggc ggccu                                          25
```

```
<210> SEQ ID NO 3
<211> LENGTH: 22
<212> TYPE: RNA
<213> ORGANISM: Homo sapiens

<400> SEQUENCE: 3
acucaaaaug ggggcgcuuu cc                                             22

<210> SEQ ID NO 4
<211> LENGTH: 23
<212> TYPE: RNA
<213> ORGANISM: Homo sapiens

<400> SEQUENCE: 4
aggaccugcg ggacaagauu cuu                                            23

<210> SEQ ID NO 5
<211> LENGTH: 21
<212> TYPE: RNA
<213> ORGANISM: Homo sapiens

<400> SEQUENCE: 5
ucguaccgug aguaauaaug c                                              21

<210> SEQ ID NO 6
<211> LENGTH: 21
<212> TYPE: RNA
<213> ORGANISM: Homo sapiens

<400> SEQUENCE: 6
agugguuuua cccuauggua g                                              21

<210> SEQ ID NO 7
<211> LENGTH: 23
<212> TYPE: RNA
<213> ORGANISM: Homo sapiens

<400> SEQUENCE: 7 agugggaac ccuuccauga gga                                             23

<210> SEQ ID NO 8
<211> LENGTH: 21
<212> TYPE: RNA
<213> ORGANISM: Homo sapiens

<400> SEQUENCE: 8
agggcccccc cucaauccug u                                              21

<210> SEQ ID NO 9
<211> LENGTH: 23
<212> TYPE: RNA
<213> ORGANISM: Homo sapiens

<400> SEQUENCE: 9
cccaguguuc agacuaccug uuc                                            23

<210> SEQ ID NO 10
<211> LENGTH: 529
<212> TYPE: RNA
<213> ORGANISM: Homo sapiens

<400> SEQUENCE: 10
augcgcccug ccuggccccc accugguccu cuuuccuuuu cagguggagg agaugccgcu    60
```

```
gucccgucgg ucuggggaca gcccagcucc ccggaucccg ggcuggagag acgcgucgcg    120
gccccggggc cugguggcac gagcaggaag gaggacccgg cggcgggcuc ugccugggcu    180
ugccugggcu uguuccgagc cgggcugcuu cucggugacc acgcagaucg ggggcauuug    240
gagauuuugc gggaguccug cagccaagcu ccggggcagg agaggccugg aagccugcac    300
uaccugcucg ccccguccca gcaugcaccc aggugcuggg gagaggcagg acaggccugu    360
cccccgaguc cccuccggau gccguggacc ggccagcugu gaguguuucu uuggcagugu    420
cuuagcuggu uguugugagc aauaguaagg aagcaaucag caaguauacu gcccuagaag    480
ugcugcacgu ugugggggccc aagagggaag augaagcgag agaugccca              529
```

<210> SEQ ID NO 11
<211> LENGTH: 20
<212> TYPE: RNA
<213> ORGANISM: Homo sapiens

<400> SEQUENCE: 11

```
gggcuugccu gggcuuguuc                                                20
```

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12

```
tttaagctta tgcgccctgc c                                              21
```

<210> SEQ ID NO 13
<211> LENGTH: 19
<212> TYPE: DNA
<213> ORGANISM: Artificial Sequence
<220> FEATURE:
<223> OTHER INFORMATION: Synthetic

<400> SEQUENCE: 13

```
ctcggtgacc acgcagatc                                                 19
```

<210> SEQ ID NO 14
<211> LENGTH: 17
<212> TYPE: DNA
<213> ORGANISM: Artificial Sequence
<220> FEATURE:
<223> OTHER INFORMATION: Synthetic

<400> SEQUENCE: 14

```
cagcatgcac ccaggtg                                                   17
```

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15

```
ttgctcacaa caaccagcta aga                                            23
```

<210> SEQ ID NO 16
<211> LENGTH: 22
<212> TYPE: DNA

```
<213> ORGANISM: Artificial Sequence
<220> FEATURE:
<223> OTHER INFORMATION: Synthetic

<400> SEQUENCE: 16
tttctcgagt gggcatctct cg                                           22

<210> SEQ ID NO 17
<211> LENGTH: 28
<212> TYPE: DNA
<213> ORGANISM: Artificial Sequence
<220> FEATURE:
<223> OTHER INFORMATION: Synthetic

<400> SEQUENCE: 17
tttctcgaga gagcttccga agtcctgg                                     28

<210> SEQ ID NO 18
<211> LENGTH: 32
<212> TYPE: DNA
<213> ORGANISM: Artificial Sequence
<220> FEATURE:
<223> OTHER INFORMATION: Synthetic

<400> SEQUENCE: 18
tttctcgagc acctgggtag cattcgcttc cc                                32

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
tttaagcttc gcgcgttcac ctcg                                         24

<210> SEQ ID NO 20
<211> LENGTH: 27
<212> TYPE: DNA
<213> ORGANISM: Artificial Sequence
<220> FEATURE:
<223> OTHER INFORMATION: Synthetic

<400> SEQUENCE: 20
agtgtttctt ccggagagtc ttagctg                                      27

<210> SEQ ID NO 21
<211> LENGTH: 27
<212> TYPE: DNA
<213> ORGANISM: Artificial Sequence
<220> FEATURE:
<223> OTHER INFORMATION: Synthetic

<400> SEQUENCE: 21
cagctaagac tctccggaag aaacact                                      27

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
acgcttgtgt ttctcagtcc g                                            21
```

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
tggtctagtt cccgcctcct                                                    20

<210> SEQ ID NO 24
<211> LENGTH: 21
<212> TYPE: DNA
<213> ORGANISM: Artificial Sequence
<220> FEATURE:
<223> OTHER INFORMATION: Synthetic

<400> SEQUENCE: 24
ggagacagga gacctctaaa g                                                  21

<210> SEQ ID NO 25
<211> LENGTH: 24
<212> TYPE: DNA
<213> ORGANISM: Artificial Sequence
<220> FEATURE:
<223> OTHER INFORMATION: Synthetic

<400> SEQUENCE: 25
cagagtaaga ggctaaggtt tacc                                               24

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
aaaagcgggg agaaagtagg                                                    20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ctagcctccc gggtttctct                                                    20

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
tgacactggc aaaacaatgc a                                                  21

<210> SEQ ID NO 29
<211> LENGTH: 21
<212> TYPE: DNA
<213> ORGANISM: Artificial Sequence
<220> FEATURE:

<223> OTHER INFORMATION: Synthetic

<400> SEQUENCE: 29
ggtccttttc accagcaagc t					21

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
gtcggagtca acggatttgg					20

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
aaaagcagcc ctggtgacc					19

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
cccaagcaat ggatgatttg a					21

<210> SEQ ID NO 33
<211> LENGTH: 21
<212> TYPE: DNA
<213> ORGANISM: Artificial Sequence
<220> FEATURE:
<223> OTHER INFORMATION: Synthetic

<400> SEQUENCE: 33
ggcattctgg gagcttcatc t					21

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
ggcagaccag catgacagat t					21

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
gcggattagg gcttcctctt					20

-continued

```
<210> SEQ ID NO 36
<211> LENGTH: 23
<212> TYPE: DNA
<213> ORGANISM: Artificial Sequence
<220> FEATURE:
<223> OTHER INFORMATION: Synthetic

<400> SEQUENCE: 36
aacaaccagc taagacactg cca                                              23

<210> SEQ ID NO 37
<211> LENGTH: 22
<212> TYPE: DNA
<213> ORGANISM: Artificial Sequence
<220> FEATURE:
<223> OTHER INFORMATION: Synthetic

<400> SEQUENCE: 37
gtgtaacacg tctatacgcc ca                                               22

<210> SEQ ID NO 38
<211> LENGTH: 23
<212> TYPE: RNA
<213> ORGANISM: Homo sapiens

<400> SEQUENCE: 38
auuugccaua gaguacacug ccu                                              23

<210> SEQ ID NO 39
<211> LENGTH: 19
<212> TYPE: RNA
<213> ORGANISM: Homo sapiens

<400> SEQUENCE: 39
cagaccgcgg gcacugccg                                                   19

<210> SEQ ID NO 40
<211> LENGTH: 62
<212> TYPE: RNA
<213> ORGANISM: Homo sapiens

<400> SEQUENCE: 40
caguaagauc acuguuuaga uuugccauag aguacacugc cugccuuaag ugaggaaauc      60
aa                                                                     62

<210> SEQ ID NO 41
<211> LENGTH: 59
<212> TYPE: RNA
<213> ORGANISM: Homo sapiens

<400> SEQUENCE: 41
gaauggagua caucguauag cagaccgcgg gcacugccgc cgcuagguag agucugagg       59

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
ctgggatgcc tttgtggaac                                                  20

<210> SEQ ID NO 43
```

```
<211> LENGTH: 19
<212> TYPE: DNA
<213> ORGANISM: Artificial Sequence
<220> FEATURE:
<223> OTHER INFORMATION: Synthetic

<400> SEQUENCE: 43
atcaaacaga ggccgcatg                                                   19

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
gtcggagtca acggatttgg                                                  20

<210> SEQ ID NO 45
<211> LENGTH: 19
<212> TYPE: DNA
<213> ORGANISM: Artificial Sequence
<220> FEATURE:
<223> OTHER INFORMATION: Synthetic

<400> SEQUENCE: 45
aaaagcagcc ctggtgacc                                                   19

<210> SEQ ID NO 46
<211> LENGTH: 90
<212> TYPE: RNA
<213> ORGANISM: Homo sapiens

<400> SEQUENCE: 46
gugaguguuu cuuuggcagu gucuuagcug guuguuguga gcaauaguaa ggaagcaauc      60
agcaaguaua cugcccuaga agugcugcac                                       90

<210> SEQ ID NO 47
<211> LENGTH: 91
<212> TYPE: RNA
<213> ORGANISM: Homo sapiens

<400> SEQUENCE: 47
gcgcggcagg gaucgcgggc ggguggcggc cuagggcgcg gagggcggac cgggaauggc      60
gcgccgugcg ccgccggcgu aacugcggcg c                                     91

<210> SEQ ID NO 48
<211> LENGTH: 87
<212> TYPE: RNA
<213> ORGANISM: Homo sapiens

<400> SEQUENCE: 48
gcucauacug ggauacucaa aauggggggcg cuuuccuuuu ugucuguacu gggaagugcu     60
ucgauuuugg ggugucccug uuugagu                                          87

<210> SEQ ID NO 49
<211> LENGTH: 116
<212> TYPE: RNA
<213> ORGANISM: Homo sapiens

<400> SEQUENCE: 49
caacuacagc cacuacuaca ggaccaucga ggaccugcgg gacaagauuc uuggugccac      60
```

```
cauugagaac gccaggauug uccugcagau caacaaugcu caacuggcug cagaug         116

<210> SEQ ID NO 50
<211> LENGTH: 83
<212> TYPE: RNA
<213> ORGANISM: Homo sapiens

<400> SEQUENCE: 50
gcuggcgacg ggacauuauu acuuuuggua cgcgcuguga cacuucaaac ucguaccgug      60
aguaauaaug cgccguccac ggc                                             83

<210> SEQ ID NO 51
<211> LENGTH: 118
<212> TYPE: RNA
<213> ORGANISM: Homo sapiens

<400> SEQUENCE: 51
gcgcccugug ugugucucuc ucuguguccu gccagugguu uacccuaug guagguuacg       60 ucaugcuguu cuaccacagg guagaaccac ggacaggaua ccggggcacc cucugcgu       118

<210> SEQ ID NO 52
<211> LENGTH: 84
<212> TYPE: RNA
<213> ORGANISM: Homo sapiens

<400> SEQUENCE: 52
uugacuuagc uggguagugg ggaacccuuc caugaggagu agaacacucc uuaugcaaga      60
uucccuucua ccuggcuggg uugg                                            84

<210> SEQ ID NO 53
<211> LENGTH: 80
<212> TYPE: RNA
<213> ORGANISM: Homo sapiens

<400> SEQUENCE: 53
aggacccuuc cagagggccc ccccucaauc cuguugugcc uaauucagag gguugggugg      60
aggcucuccu gaagggcucu                                                 80

<210> SEQ ID NO 54
<211> LENGTH: 83
<212> TYPE: RNA
<213> ORGANISM: Homo sapiens

<400> SEQUENCE: 54
ggccccgcca acccaguguu cagacuaccu guucaggagg cucucaaugu guacaguagu      60
cugcacauug guuaggcugg gcu                                             83
```